(12) United States Patent
Hiranuma et al.

(10) Patent No.: US 7,896,213 B2
(45) Date of Patent: Mar. 1, 2011

(54) MEDICAL STAPLER WITH LATCHING GRIP PORTION

(75) Inventors: Toshio Hiranuma, Tokyo (JP);
Masahiko Hashimoto, Tokyo (JP);
Shigenori Yamaguchi, Tokyo (JP);
Yutaka Kato, Tokyo (JP)

(73) Assignee: Max Co., Ltd., Tokyo (JP)

( * ) Notice: Subject to any disclaimer, the term of this patent is extended or adjusted under 35 U.S.C. 154(b) by 204 days.

(21) Appl. No.: 12/306,471

(22) PCT Filed: Jun. 19, 2007

(86) PCT No.: PCT/JP2007/062300
§ 371 (c)(1),
(2), (4) Date: Dec. 23, 2008

(87) PCT Pub. No.: WO2008/001645
PCT Pub. Date: Jan. 3, 2008

(65) Prior Publication Data
US 2009/0277945 A1   Nov. 12, 2009

(30) Foreign Application Priority Data

Jun. 30, 2006 (JP) ................................ 2006-182370
Dec. 18, 2006 (JP) ................................ 2006-340593
Jan. 26, 2007 (JP) ................................ 2007-015988

(51) Int. Cl.
*A61B 17/10* (2006.01)
(52) U.S. Cl. ..................... 227/176.1; 227/175.1; 227/19
(58) Field of Classification Search ............... 227/176.1, 227/19, 175.1
See application file for complete search history.

(56) References Cited

U.S. PATENT DOCUMENTS

| 4,520,817 | A | * | 6/1985 | Green | 227/176.1 |
| 4,605,001 | A | * | 8/1986 | Rothfuss et al. | 227/178.1 |
| 4,608,981 | A | * | 9/1986 | Rothfuss et al. | 227/180.1 |
| 4,662,555 | A | | 5/1987 | Thornton | |
| 5,074,454 | A | * | 12/1991 | Peters | 227/178.1 |
| 5,156,315 | A | * | 10/1992 | Green et al. | 227/178.1 |
| 5,379,933 | A | * | 1/1995 | Green et al. | 227/176.1 |
| 5,489,058 | A | * | 2/1996 | Plyley et al. | 227/176.1 |

(Continued)

FOREIGN PATENT DOCUMENTS

JP         58-80212         5/1983

(Continued)

*Primary Examiner* — Brian D Nash
(74) *Attorney, Agent, or Firm* — Drinker Biddle & Reath LLP

(57) ABSTRACT

A medical stapler is provided with a stapler body having a head portion at one end thereof, which drives out medical staples S, and a manipulating lever that can be opened and closed by being turned in a state in which a part provided at the side of the head portion is housed in an accommodating portion of the stapler body. A grip portion opposed to the head portion of the manipulating lever is usually urged in an opening direction in which the grip portion protrudes from the accommodating portion. When a staple S is driven out, the manipulating lever is turned in a closing direction in which the manipulating lever is housed in the accommodating portion. Thus, the staple S is driven out of the head portion. Then, the staple S is put into skin "a" while both sides of a wound are brought toward each other. Thus, the wound is sutured while both tip end parts of the staple are inwardly bent. Upon completion of suturing the wound, the manipulating lever is latched in the stapler body in a state in which the staple S is bent.

10 Claims, 36 Drawing Sheets

U.S. PATENT DOCUMENTS 7,059,509 B2 6/2006 Brown

FOREIGN PATENT DOCUMENTS

| JP | 60-68841 | 4/1985 |
| --- | --- | --- |
| JP | 62-243545 | 10/1987 |
| JP | 5-154159 | 6/1993 |
| JP | 3054202 | 4/2000 |
| JP | 2005-334206 | 12/2005 |
| JP | 2006-6816 | 1/2006 |

* cited by examiner

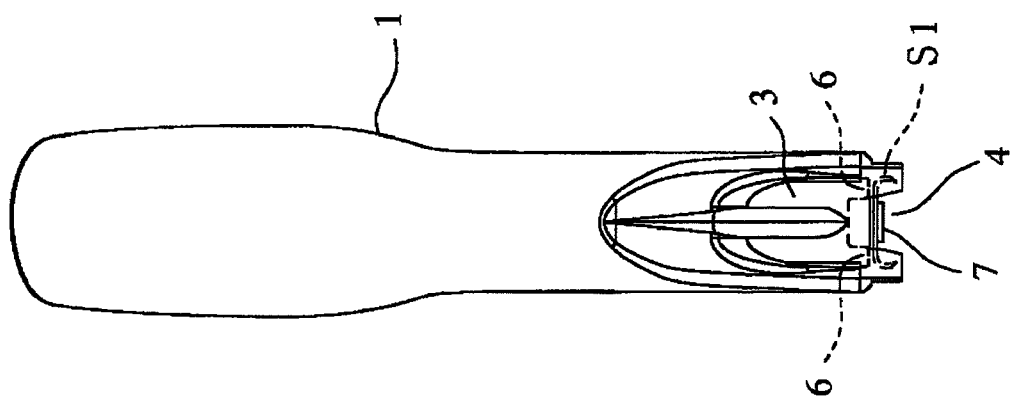
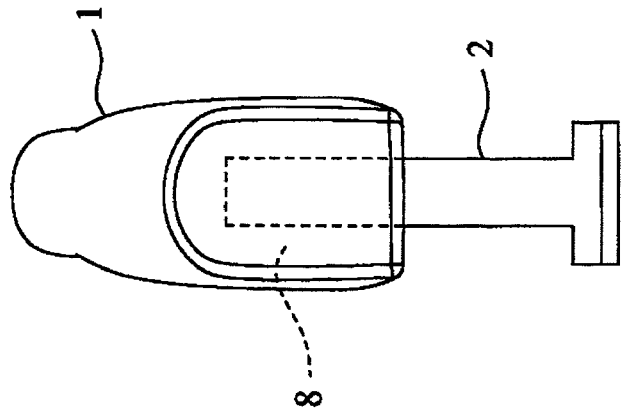

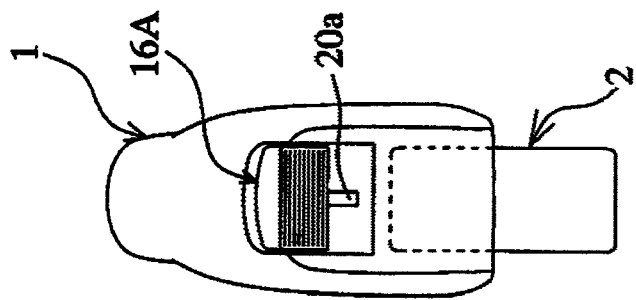
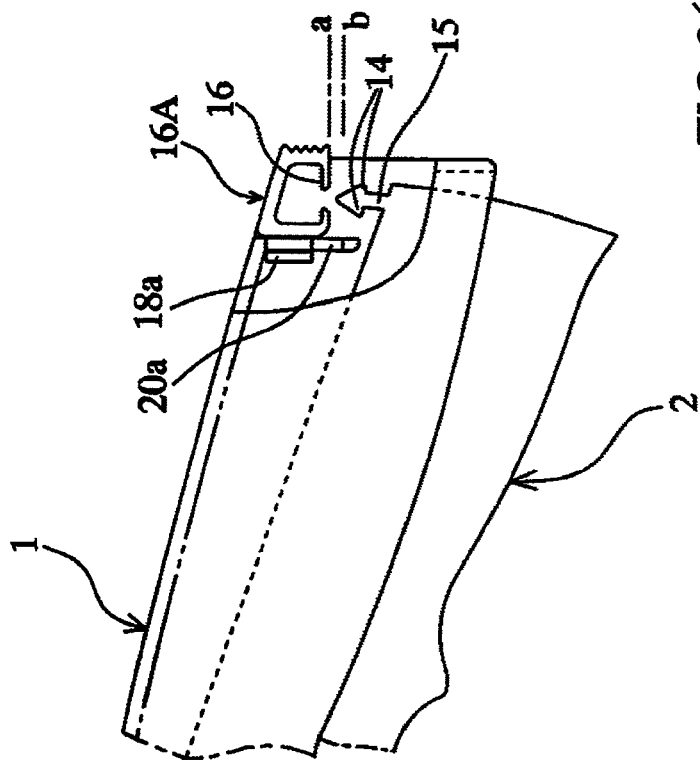
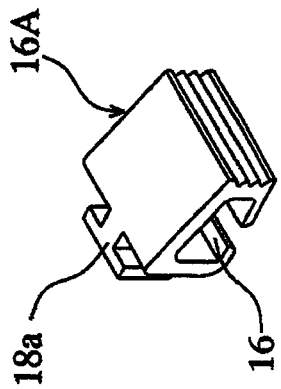

FIG.11(a)
FIG.11(c)
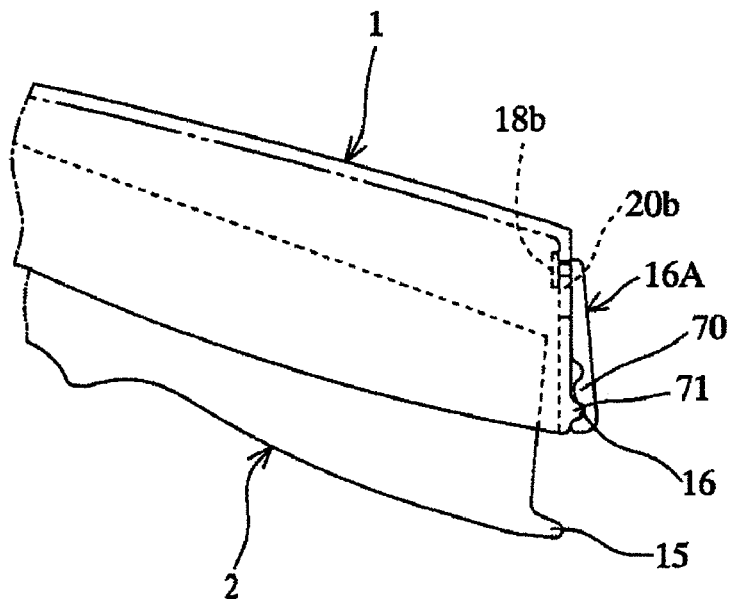
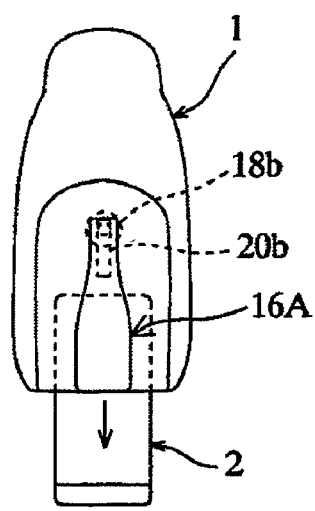
FIG.11(c)
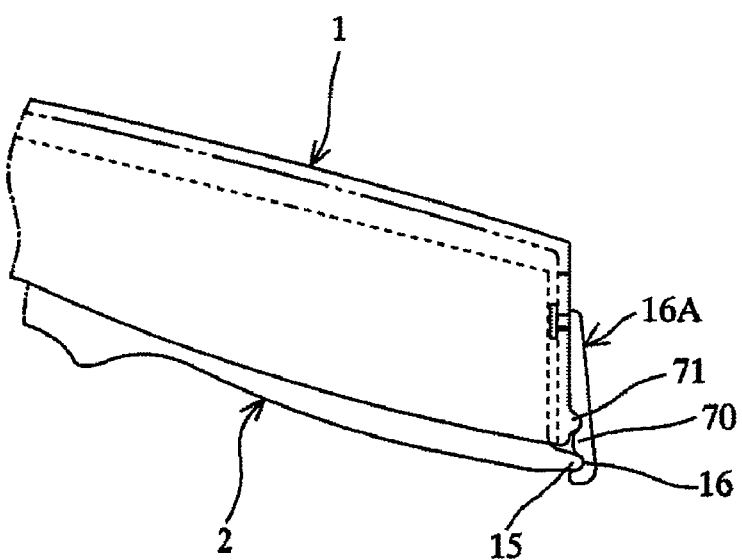

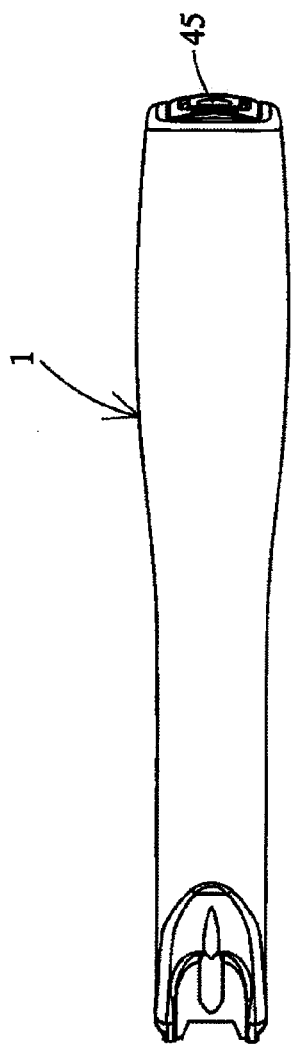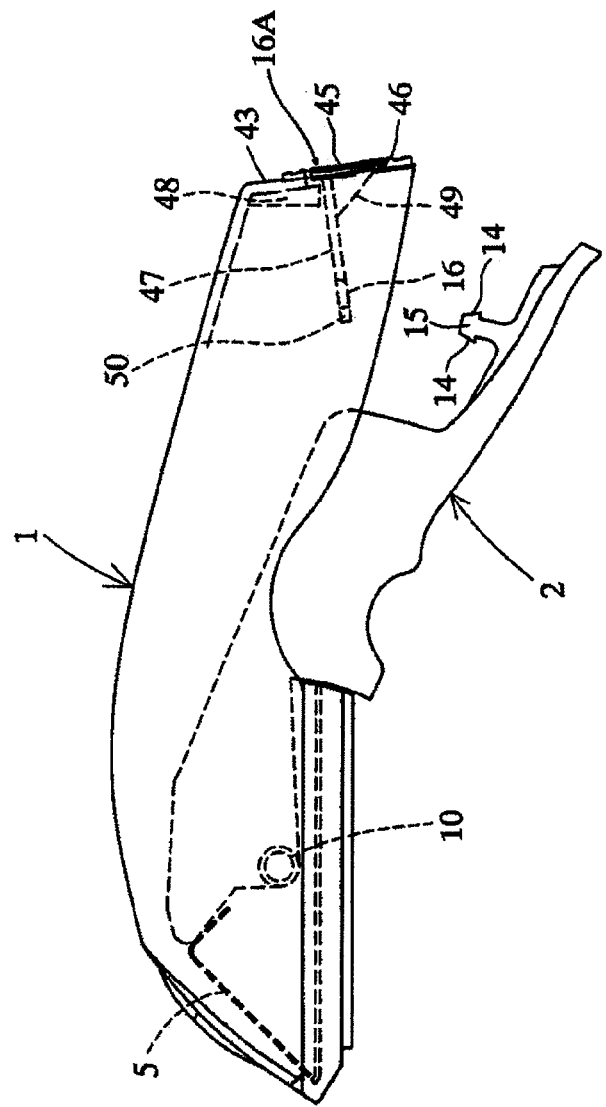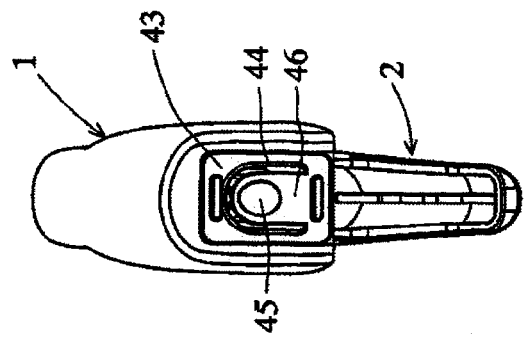

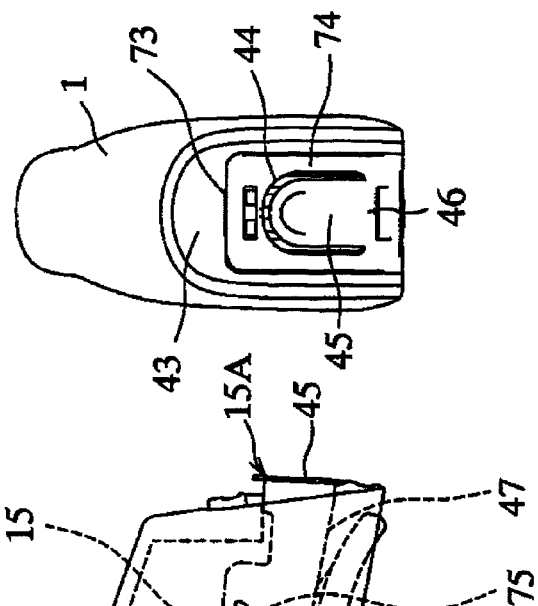
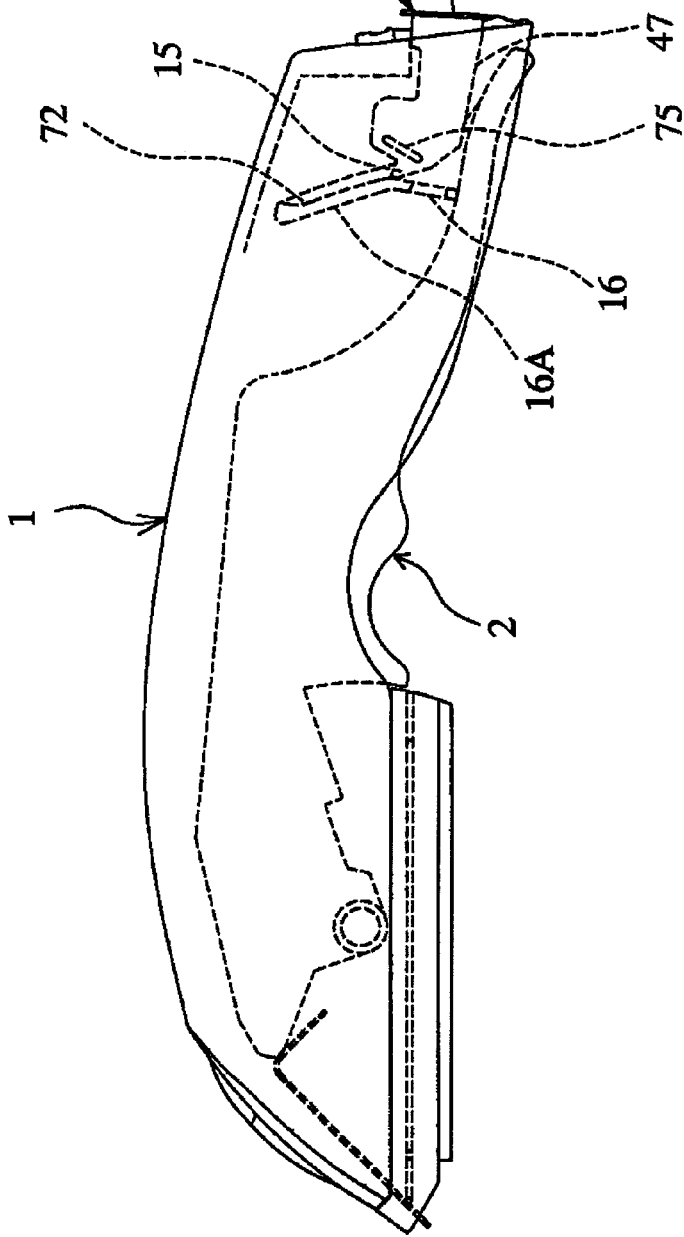

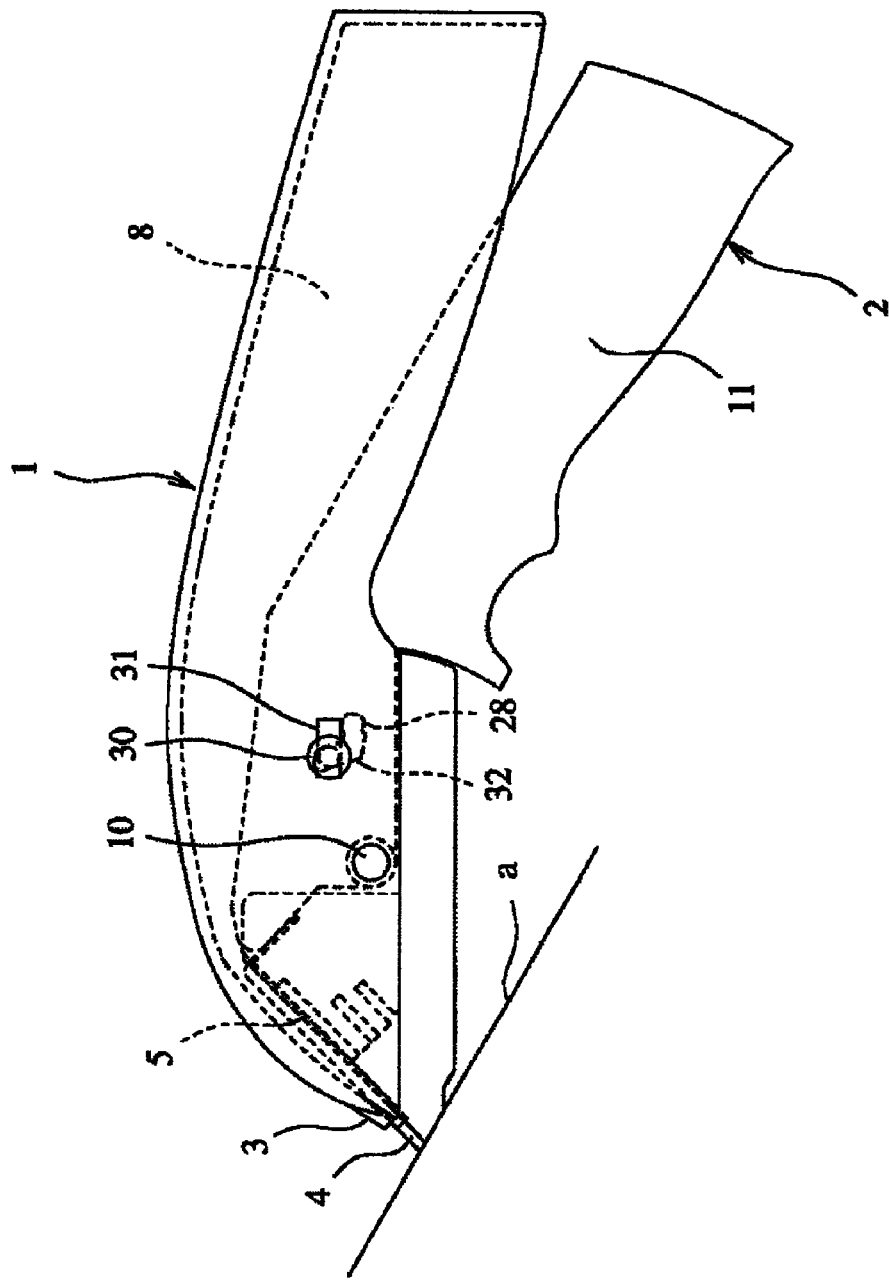
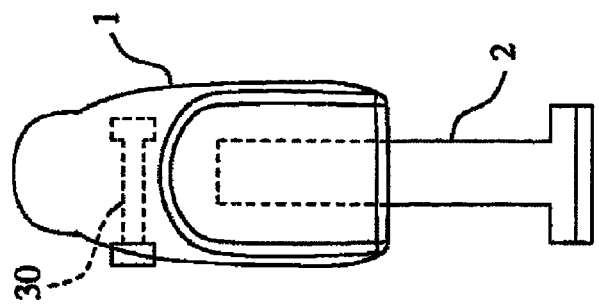

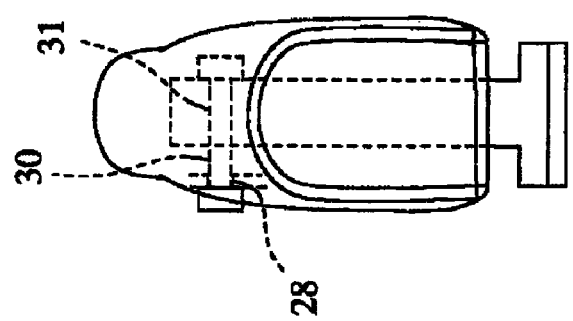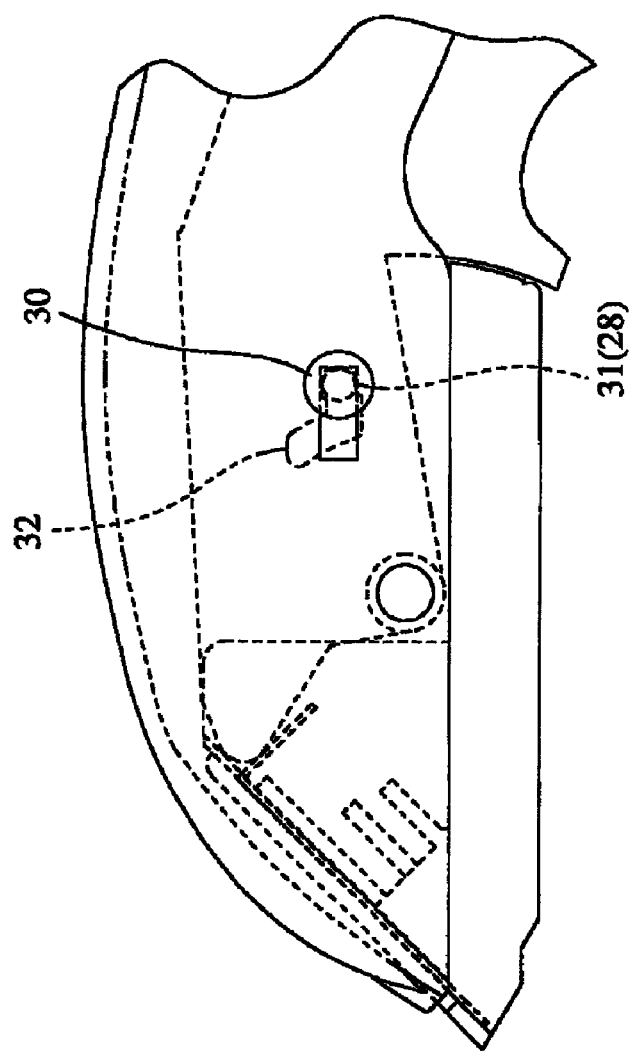

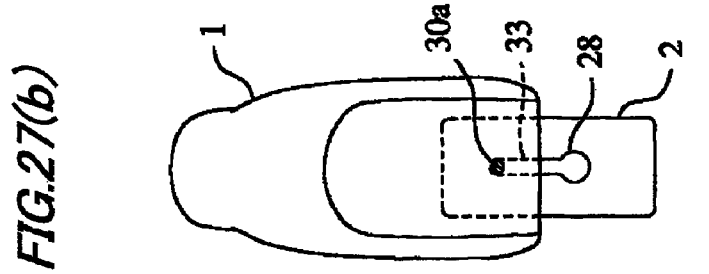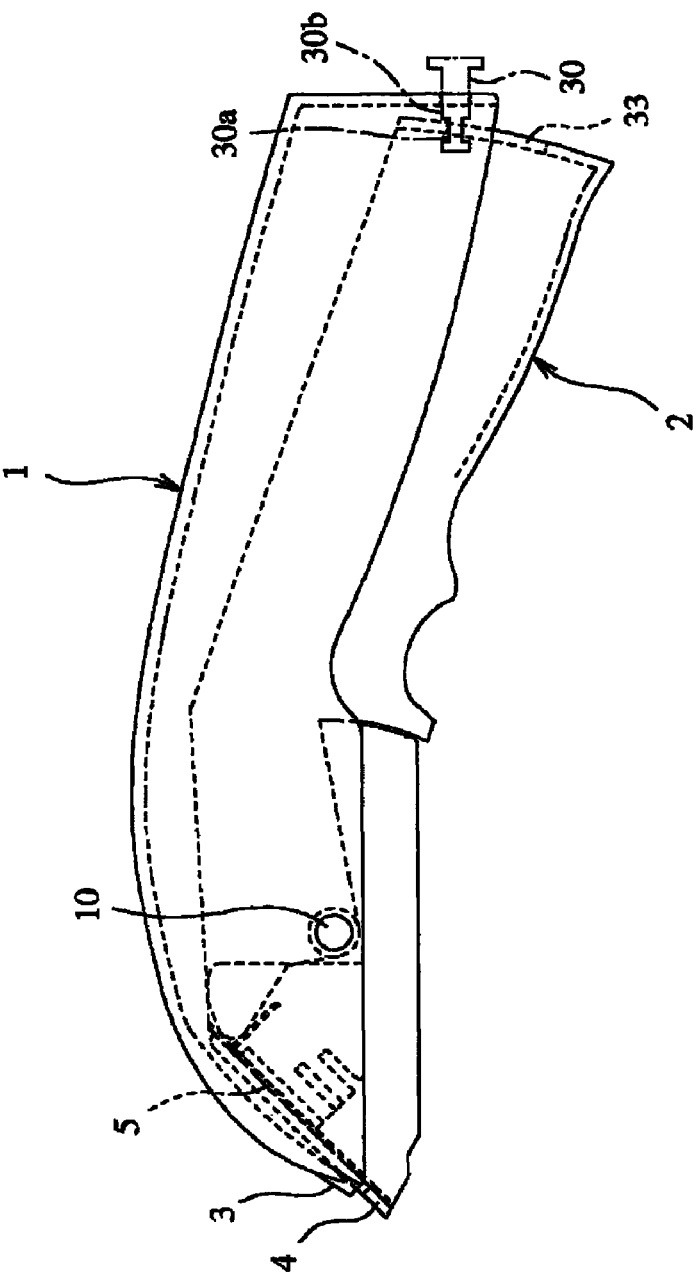

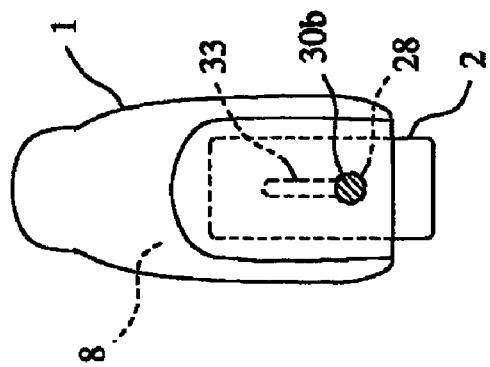
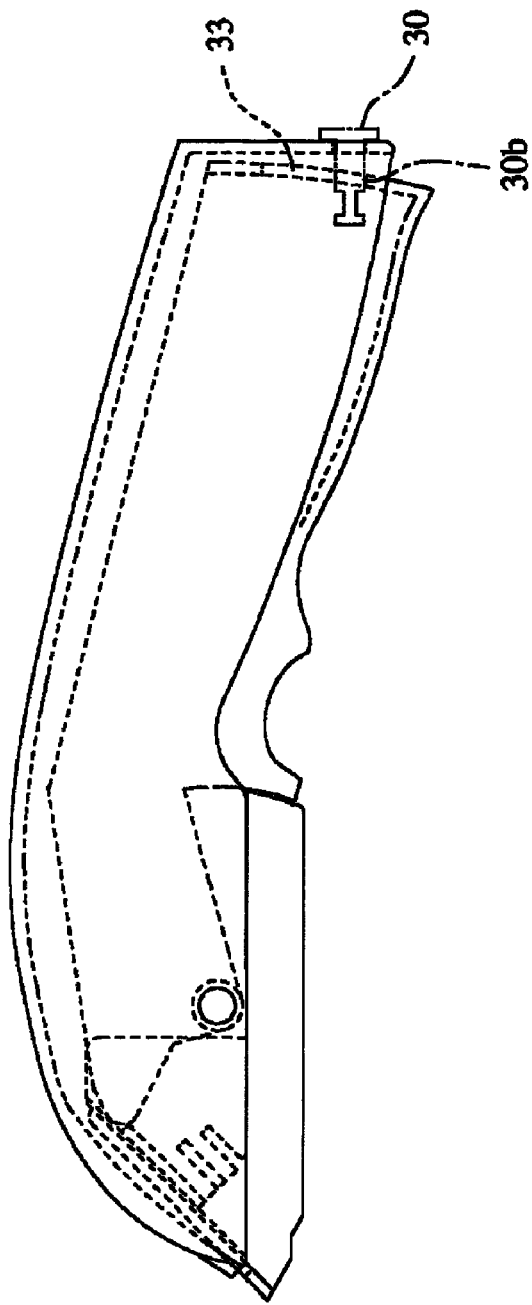
FIG.28(a)
FIG.28(b)

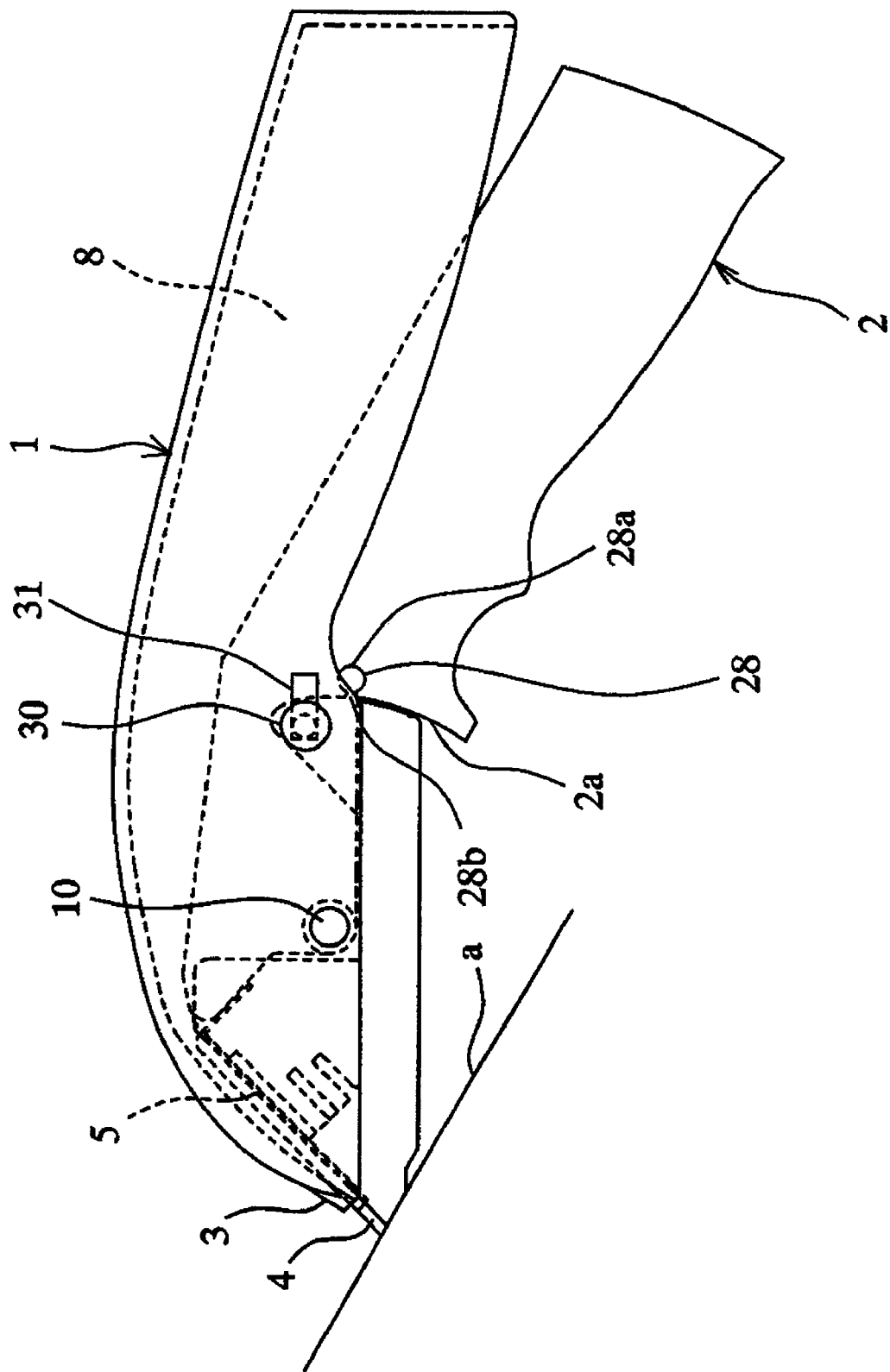

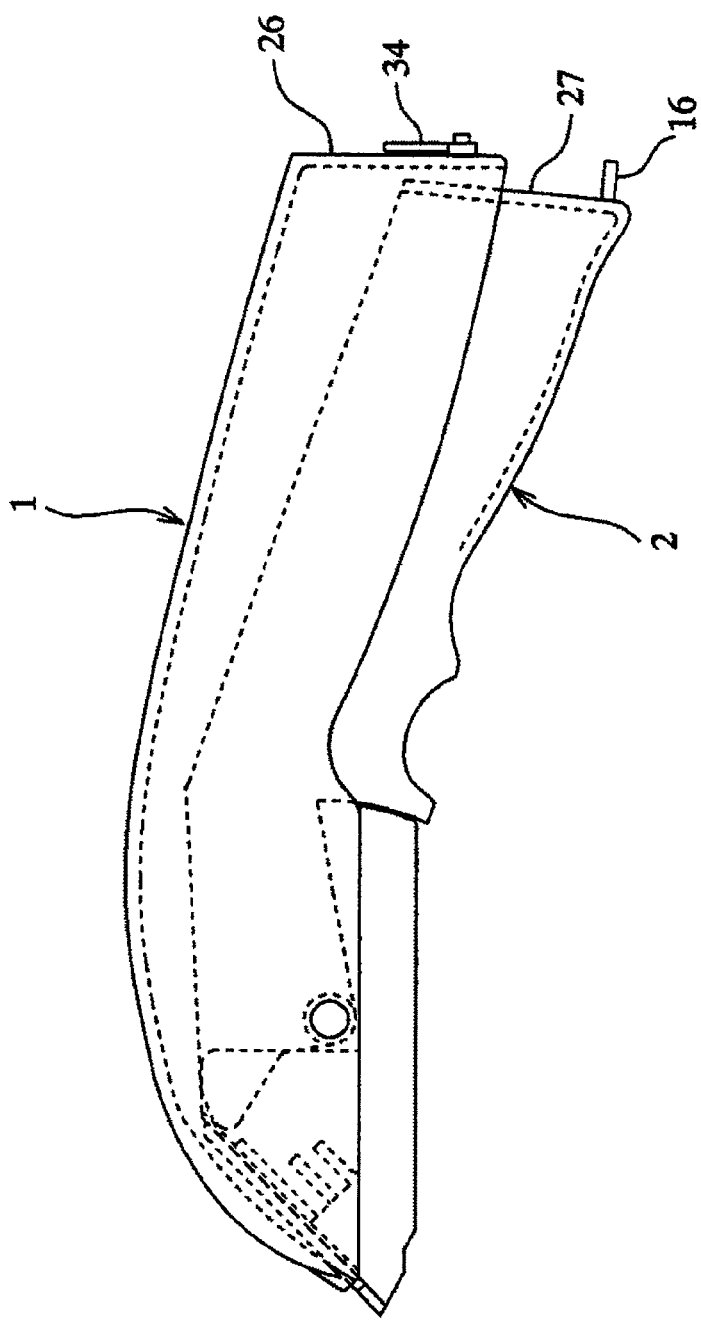
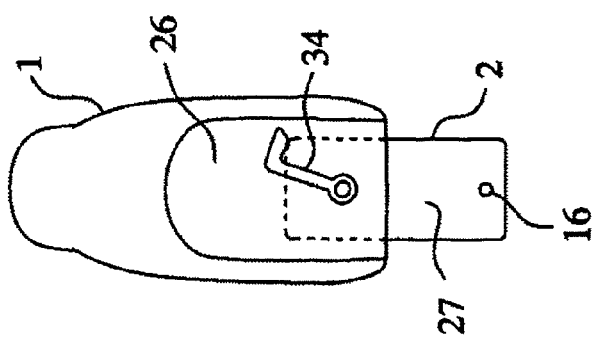

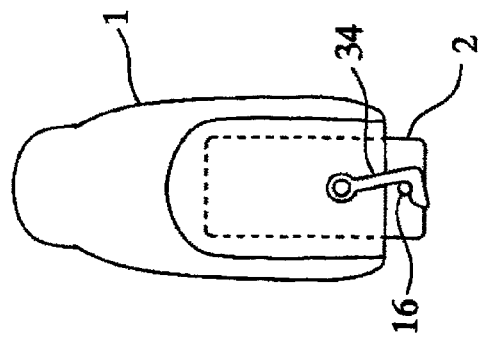
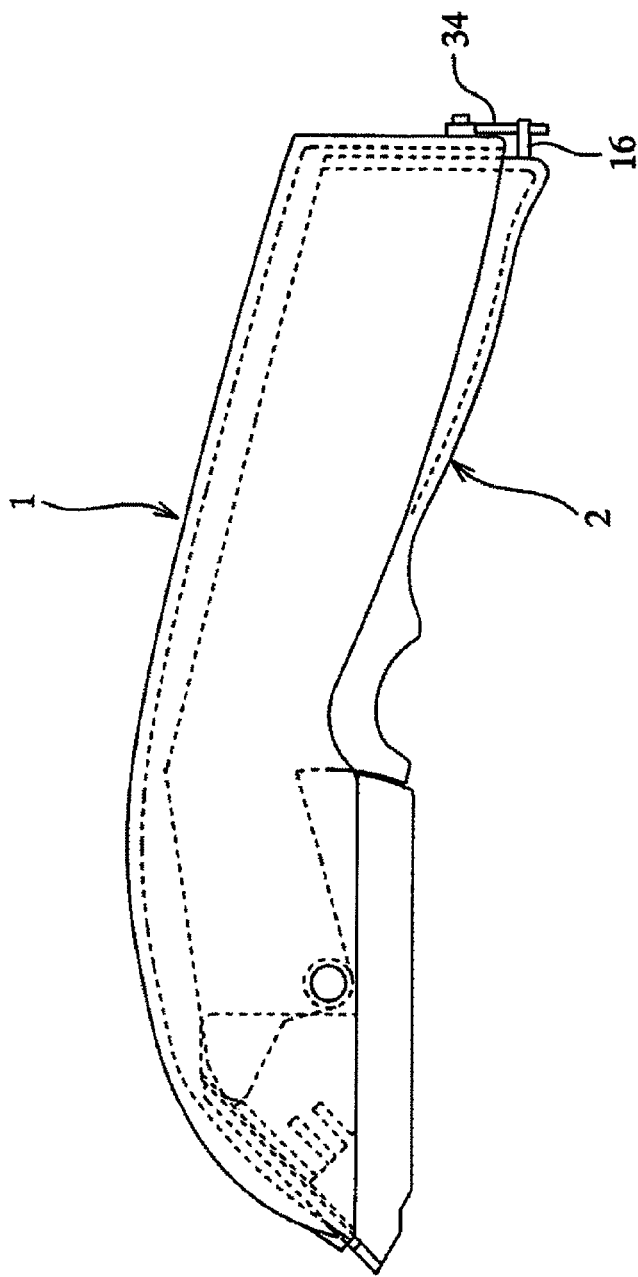

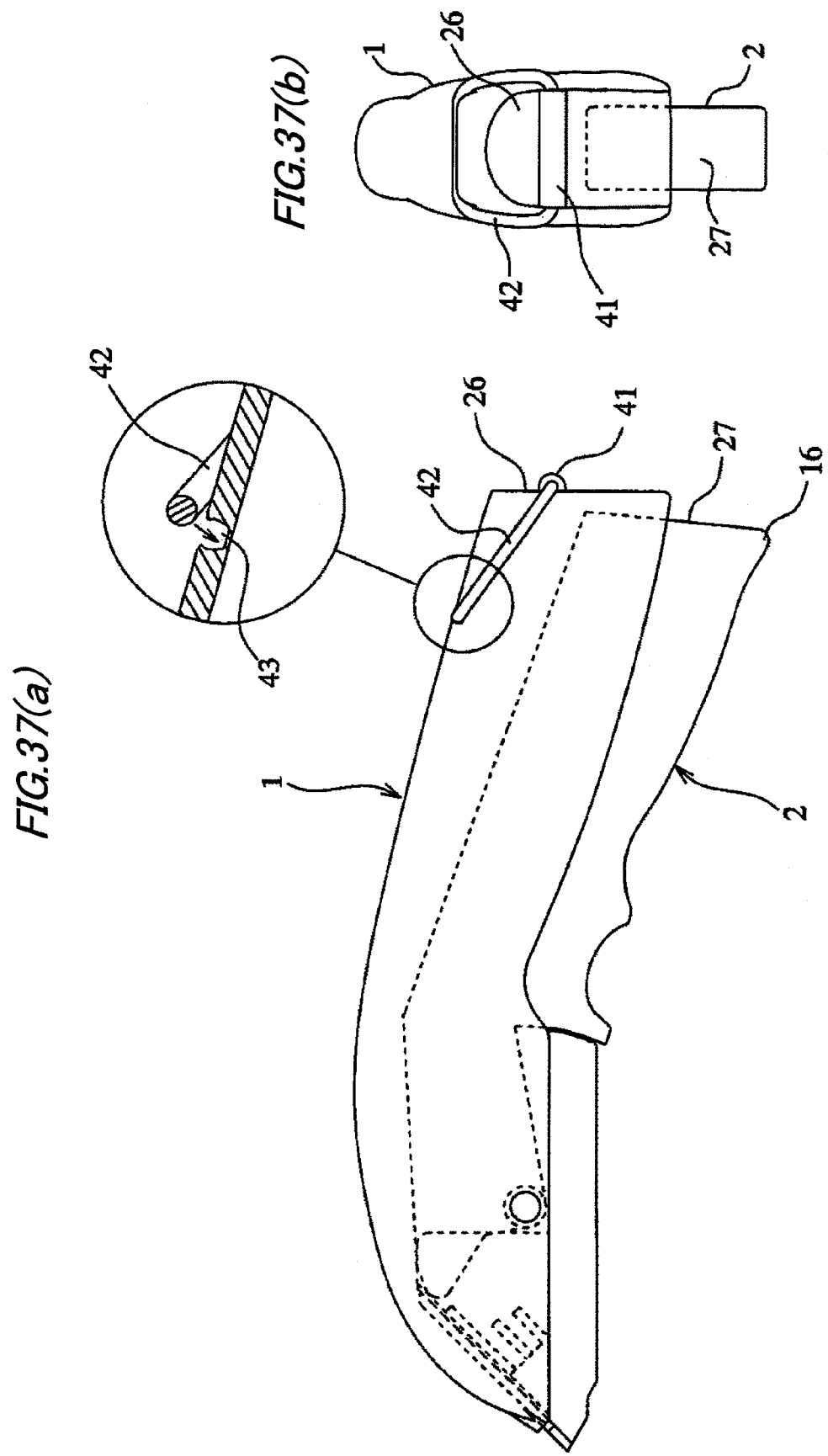

MEDICAL STAPLER WITH LATCHING GRIP PORTION

TECHNICAL FIELD

The present invention relates to a medical stapler used for suturing a wound.

BACKGROUND ART

Generally, as means for suturing a wound in a surgical operation, medical staples are used, in addition to suture-threads (see, e.g., JP-B2-3054202). The medical staple consists of a crown portion and staple leg portions that extend in a curved manner downwardly from curved parts at both sides of the crown portion, respectively. The medical staples are used by means of a medical stapler. The medical stapler has a stapler body having a head portion loaded with staples and has also a manipulating lever turnably attached to the stapler body. Usually, the manipulating lever is preliminarily urged in an opening direction in which the manipulating lever is spaced from the stapler body. In order to suture a wound, a user strongly grips and turns the manipulating lever in a closing direction. Thus, the medical staple is protruded from the head portion. Then, the medical staple is put into skin, while both sides of the wound are brought toward each other.

The wound is sutured by inwardly bending both tip end parts of the medical staple.

In a case where a wound is sutured using a suture-thread, the wound between threading holes formed in both sides thereof is bound with the suture thread. Accordingly, even after removal of the suture-thread, it is often that a scar of the thread is left on skin. On the other hand, in a case where a wound is sutured using a medical staple, the crown portion of the medical staple is not contacted with skin. Consequently, after removal of the medical stapler is removed, only the scar of the wound is left on the skin. Thus, generally, an operative scar is neat. Accordingly, a suturing operation using a medical stapler is expected to become widespread.

Meanwhile, basically, medical staplers are disposable.

Accordingly, upon completion of a suturing operation, medical staplers are discarded, regardless of how many medical staples are left in the medical stapler.

However, even when a medical stapler is discarded without performing processing thereon after a suturing operation is finished (i.e., after the medical stapler is used), the manipulating lever is put into an open state with respect to the stapler body urged in an opening direction. Thus, the manipulating lever is in a bulky state in which the manipulating lever is largely spaced from the stapler body and protrudes from the stapler body. The cost of disposal of medical waste, from which persons are at risk of infection, is higher than that of disposal of ordinary waste. Reduction of the volume of waste is a major problem in reducing the expenditure of a hospital and the cost of disposal of waste.

Further, in a suturing operation, all medical staples loaded in a medical stapler are not always used. Sometimes, medical staples remain in a medical stapler that is to be discarded.

Thus, the problem of poor hygiene is caused as follows. That is, when an external force is applied to the manipulating lever in the middle of disposal of a garbage bag containing a medical stapler, a staple driven out of this medical stapler breaks through the garbage bag. Thus, the medical staple contaminated with the body fluid of a patient is exposed.

As a countermeasure to such a problem, there is provided a method for driving out all of medical staples left in a medical stapler as wastes and then individually discarding the medical staples and the medical stapler. However, this method has the following problems. That is, an operating room is contaminated with unnecessary medical staples driven out as wastes. In addition, this method causes a situation in which the medical staples driven out as wastes accidentally adhere to a patient.

Additionally, another method for disassembling a medical stapler and then discarding the medical stapler is considered.

However, this method is inconvenient in that fine staples should be treated when the medical stapler is disassembled.

In addition, there is a fear that fine components are scattered in the operating room during the operation. Thus, this method is not an effective means.

DISCLOSURE OF THE INVENTION

One or more embodiments of the invention provide a medical stapler capable of achieving volume reduction of a medical waste and simply and surely performing processing of residual staples by discarding the medical stapler in a state in which a manipulating lever is closed.

According to one or more embodiments of the invention and to a first aspect of the invention, there is provided a medical stapler includes a stapler body having a head portion provided at one end thereof to drive out a medical staple, and a manipulating lever provided to be pivotally supported by the stapler body to be closable and openable. A grip portion placed at a side of the manipulating lever, which is opposite to a side thereof corresponding to the head portion, is urged in an opening direction in which the grip portion is moved apart from the stapler body. When the medical staple is driven out, the manipulating lever is turned in a closing direction, in which the manipulating lever is moved closer to the stapler body, to protrude the staple from the head portion to suture a wound while both side tip end portions of the staple are inwardly bent. The manipulating lever is enabled to be latched in the stapler body in a state, in which the manipulating lever is turned in a closing direction of bending the medical staple, upon completion of suturing of the wound.

According to a second aspect of the invention, the latch portion provided on the manipulating lever can be latched to the latch receiving portion by turning, when the manipulating lever is turned in the closing direction upon completion of the suturing of the wound, the manipulating lever over a movable range to elastically deform the manipulating lever.

According to a third aspect of the invention, the latch portion is formed at one of the stapler body and the manipulating lever. The latch receiving portion is formed in the other of the stapler body and the manipulating lever. In addition, the latch portion or the latch receiving portion provided at one of the stapler body and the manipulating lever can be configured to be operated to a standby position, at which the latch portion or the latch receiving portion is prevented from being latched to the latch receiving portion or the latch portion provided at the other of the stapler body and the manipulating lever and to a latchable position at which the latch portion or the latch receiving portion is allowed to be latched to the latch receiving portion or the latch portion provided at the other of the stapler body and the manipulating lever.

According to a fourth aspect of the invention, the medical stapler can be configured to include an operating portion provided on an outer surface of the stapler body, and one of the latch portion and the latch receiving portion, which is provided in a latch piece portion extended from the operating portion to an inner side of the stapler body, so that the latch piece portion can be operated to the latchable position from the standby position.

According to a fifth aspect of the invention, the operable latch portion or the operable latch receiving portion can be provided with a holding means configured to hold the latch portion or the latch receiving portion at the standby position and the latchable position.

According to a sixth aspect of the invention, latching between the latch portion and the latch receiving portion can be allowed by turning the manipulating lever in the closing direction after the operating portion is operated.

According to a seventh aspect of the invention, latching between the latch portion and the latch receiving portion can be allowed by operating the operating portion after the manipulating lever is turned in the closing direction.

According to an eighth aspect of the invention, the medical stapler has an attachable/detachable latch pin provided in one of the stapler body and the manipulating lever, and pin holes respectively formed in the stapler body and the manipulating lever. In addition, the medical stapler can be configured so that the latch pin is insertable into the two pin holes in a state in which the pin holes respectively provided in the stapler body and the manipulating lever are aligned with each other by turning the manipulating lever in the closing direction upon completion of the suturing of the wound.

According to a ninth aspect of the invention, the medical stapler can be configured to have a latch groove formed in one of the stapler body and the manipulating lever, and a slide shaft provided in the other of the stapler body and the manipulating lever so that the slide shaft is latchable in the latch groove when the manipulating lever is turned in the closing direction upon completion of the suturing of the wound.

According to a tenth aspect of the invention, the latch groove can comprise a groove bottom portion formed to have a diameter substantially equal to a shaft diameter of the slide shaft, and a narrow portion that is placed to an aperture portion and is formed to be narrower than the shaft diameter of the slide shaft. In addition, the slide shaft can be latched to the groove bottom portion by spreading the narrow portion.

According to an eleventh aspect of the invention, the medical stapler can be configured so that the latch portion is formed in one of the stapler body and the manipulating lever, that the latch receiving portion, which is latchable to the latch portion when the manipulating lever is turned in the closing direction, is formed in the other of the stapler body and the manipulating lever, and that an interference member is provided between the latch portion and the latch receiving portion to be positionable at a first position, at which latching between the latch portion and the latch receiving portion is prevented, and a second position at which the latching between the latch portion and the latch receiving portion is allowed.

According to a twelfth aspect of the invention, the medical stapler can be configured so that a latch hook is turnably provided in a rear portion of the stapler body, and that the latch hook is latched to the manipulating lever when the manipulating lever is turned in the closing direction upon completion of the suturing of the wound.

The medical stapler according to the first aspect is configured so that the manipulating lever is latchable to the stapler body in a state, in which the manipulating lever is turned in the closing direction of bending a medical staple, upon completion of the suturing of a wound. Thus, the manipulating lever is held in a state in which the manipulating lever is moved close to the stapler body. Consequently, the volume of the entire stapler is reduced. Accordingly, the volume thereof at disposal thereof can be reduced. This can contribute to reduction in the volume of medical waste.

Further, the manipulating lever is finally latched to the stapler body in a state in which the manipulating lever is turned in the closing direction of bending a medical staple.

Thus, a tip end portion of a leading one of medical staples left in the head portion is fixed therein in a state in which the top end portion is inwardly bent. Accordingly, each of the tip end portions of the medical staple does not protrude from the stapler body. Consequently, the medical staple is safely discarded. Even when an external force is applied thereto in the middle of processing of a garbage bag, there is no fear that a medical staple pushed out therefrom breaks through the garbage bag and is exposed. Thus, a disposal work can safely be performed. In addition, a medical stapler can be discarded in a state, in which remaining staples are left therein, without being disassembled. Consequently, there is no fear that the inside of an operating room is contaminated.

According to the second aspect, the latch portion provided on the manipulating lever can be latched to the latch receiving portion by turning, when the manipulating lever is turned in the closing direction upon completion of the suturing of a wound, the manipulating lever over a movable range to elastically deform the manipulating lever. Thus, a user has only to turn the manipulating lever by a grasping force whose magnitude is larger than that of a normal grasping force. Consequently, a user can easily perform a disposal work.

According to the third aspect, the latch portion or the latch receiving portion, which is formed in one of the stapler body and the manipulating lever, can be operated to the standby position, at which this latch portion or latch receiving portion is prevented from being latched to the latch receiving portion or the latch portion formed in the other of the stapler body and the manipulating lever, and the latchable position at which latching between the latch portion or the latch receiving portion formed in the one of the stapler body and the manipulating lever and the latch receiving portion or the latch portion formed in the other thereof is allowed. Thus, upon completion of the suturing of a wound, the closed state of the manipulating lever can be held by operating the latch portion or the latch receiving portion formed in the stapler body or the manipulating lever through a one-touch simple operation.

According to the fourth aspect, the latch piece portion can be operated from the standby position to the latchable position by operating the operating portion provided on the outer surface of the stapler body. Thus, unless the operating portion is operated, the latch piece portion is not operated to the latchable position. There is no fear that the manipulating lever is erroneously held in the closed state.

According to the fifth aspect, the operable latch portion or the operable latch receiving portion is provided with a holding means configured to hold the latch portion or the latch receiving portion at the standby position and the latchable position. Thus, there is no fear that the position of the latch portion or the latch receiving portion is erroneously changed to the standby position or the latchable position.

According to the sixth aspect, the latching between the latch portion and the latch receiving portion is allowed by turning the manipulating lever in the closing direction after the operating portion is operated. Thus, unless the operating portion is operated, the latching between the latch portion and the latch receiving portion is not performed even when the manipulating lever is put into a closed state. Consequently, there is no fear that the manipulating lever is erroneously held in the closed state.

According to the seventh aspect, the latching between the latch portion and the latch receiving portion is allowed by operating the operating portion after the manipulating lever is turned in the closing direction. Thus, unless the operating portion is operated after an operation of grasping the manipulating lever is performed, the latching between the latch portion and the latch receiving portion is not performed. Consequently, there is no fear that the manipulating lever is erroneously held in the closed state. Further, because the operating portion is operated after the operation of grasping the operating lever is performed, a user can successively transit the operation of grasping the manipulating lever to a disposal operation without feeling odd.

According to the eighth aspect, the closed state of the manipulating lever can be held by turning the manipulating lever in the closing direction upon completion of the suturing of a wound to detach the latch pin in a state in which the pin holes formed in the stapler body and the manipulating lever are aligned with each other, and then inserting the latch pin into the two pin holes. Moreover, because the latch pin is detachably and attachably provided in one of the stapler body and the manipulating lever, the detachment of the latch pin can easily be achieved. Consequently, an operation of the medical stapler is facilitated.

According to the ninth aspect, the medical stapler is configured so that the latch groove is formed in one of the stapler body and the manipulating lever, that the slide shaft, which is latchable in the latch groove when the manipulating lever is turned in the closing direction upon completion of the suturing of a wound, is provided in the other of the stapler body and the manipulating lever. Thus, the closed state of the manipulating lever can be held by turning the manipulating lever in the closing direction to slide the slide shaft and to latch the slide shaft in the latch groove in a case where the slide shaft is not operated in a normal suturing operation and where the disposal is performed upon completion of the suturing of a wound. Because it is unnecessary to detach the slide shaft, an operation of the stapler can be achieved extremely easily.

According to the tenth aspect, the medical stapler is configured so that the latch groove includes a groove bottom portion formed to have a diameter substantially equal to a shaft diameter of the slide shaft, and a narrow portion that is placed to the aperture portion and is formed to be narrower than the shaft diameter of the slide shaft, and that the slide shaft is latched to the groove bottom portion by spreading the narrow portion. Thus, when the medical stapler is discarded upon completion of suturing of a wound, the manipulating lever is grasped to put the stapler into the closed state in which the slide groove and the latch groove are aligned with each other. Then, the slide shaft is forcibly moved along the slide groove to the latch groove. The slide shaft is latched to the groove bottom portion after the narrow portion provided at the opening side of the latch groove is spread. Thus, the closed state of the manipulating lever can be held. Furthermore, when the slide shaft is slid in an opposite direction, it is necessary to spread the narrow portion. Consequently, there is no fear that the slide shaft is erroneously slid when a normal suturing operation is performed. Accordingly, the slide shaft is put into a state in which the slide shaft is held in the latch groove. Because it is unnecessary to detach the slide shaft, the medical stapler can easily be handled.

According to the eleventh aspect, the interference member is provided between the latch portion and the latch receiving portion to be positionable at the first position, at which latching between the latch portion and the latch receiving portion is prevented, and the second position at which the latching between the latch portion and the latch receiving portion is allowed. Thus, the latching between the latch portion and the latch receiving portion is prevented by positioning the interference member at the first position. Consequently, the manipulating lever cannot be held in the closed state. On the other hand, the latching between the latch portion and the latch receiving portion is allowed by positioning the interference member at the second position. Thus, the manipulating lever can be held in the closed state. Accordingly, unless the interference member is operated, the latch piece portion is not latched to the latchable position. Thus, there is no fear that the manipulating lever is erroneously held in the closed state.

According to the twelfth aspect, the medical stapler is configured so that the latch hook provided in the rear portion of the stapler body is latched to the manipulating lever when the manipulating lever is turned in the closing direction upon completion of the suturing of a wound. Thus, the structure of the stapler is simple. A latch operation can easily be performed.

Other aspects and advantages of the invention will be apparent from the following description and the appended claims.

BRIEF DESCRIPTION OF THE DRAWINGS

FIG. 2(a) is a front view of the medical stapler.

FIG. 2(b) is a rear view of the medical stapler.

FIG. 9(a) is a side view of a medical stapler according to another example of the second exemplary embodiment.

FIG. 9(b) is a rear view of the medical stapler illustrated in FIG. 9(a).

FIG. 9(c) is a perspective view of a latch receiving portion of the medical stapler illustrated in FIG. 9(a).

FIG. 11(a) is a side view of a part of a medical stapler according to yet another example of the second exemplary embodiment.

FIG. 11(b) is a rear view of the medical stapler illustrated in FIG. 11(a).

FIG. 11(c) is a partly side view illustrating a state of the medical stapler illustrated in FIG. 11(a), in which the medical stapler is discarded.

FIG. 12(a) is a plan view of a stapler according to yet another example of the second exemplary embodiment.

FIG. 12(b) is a front view of the stapler illustrated in FIG. 12(a).

FIG. 12(c) is a side view of the stapler illustrated in FIG. 12(a).

FIG. 17(a) is a side view illustrating another example of the second exemplary embodiment of the medical stapler.

FIG. 17(b) is a rear view of the medical stapler illustrated in FIG. 17(a).

FIG. 24(a) is a side view of a stapler according to a fourth exemplary embodiment.

FIG. 24(b) is a rear view of the stapler illustrated in FIG. 24(a).

FIG. 26(a) is an enlarged side view illustrating a state of the medical stapler illustrated in FIG. 24(a), in which the medical stapler is discarded.

FIG. 26(b) is an enlarged side view illustrating a state of the medical stapler illustrated in FIG. 24(a), in which the medical stapler is discarded.

FIG. 27(a) is a side view of a stapler according to yet another example of the fourth exemplary embodiment.

FIG. 27(b) is a rear view of the stapler illustrated in FIG. 27(a).

FIG. 28(a) is a side view illustrating a state of the medical stapler illustrated in FIG. 27(a), in which the medical stapler is discarded.

FIG. 28(b) is an enlarged side view illustrating a state of the medical stapler illustrated in FIG. 27(a), in which the medical stapler is discarded.

FIG. 29 is a rear view of a stapler according to yet another example of the fourth exemplary embodiment.

FIG. 35(a) is a side view of a stapler according to a sixth exemplary embodiment.

FIG. 35(b) is a rear view of the stapler illustrated in FIG. 35(a).

FIG. 36(a) is a side view illustrating a state in which the medical stapler illustrated in FIG. 35(a) is discarded.

FIG. 36(b) is a rear view illustrating a state in which the medical stapler illustrated in FIG. 35(a) is discarded.

FIG. 37(a) is a side view illustrating a stapler according to yet another embodiment.

FIG. 37(b) is a rear view of the stapler illustrated in FIG. 37(a).

DESCRIPTION OF REFERENCE NUMERALS AND SIGNS

Figure 1:
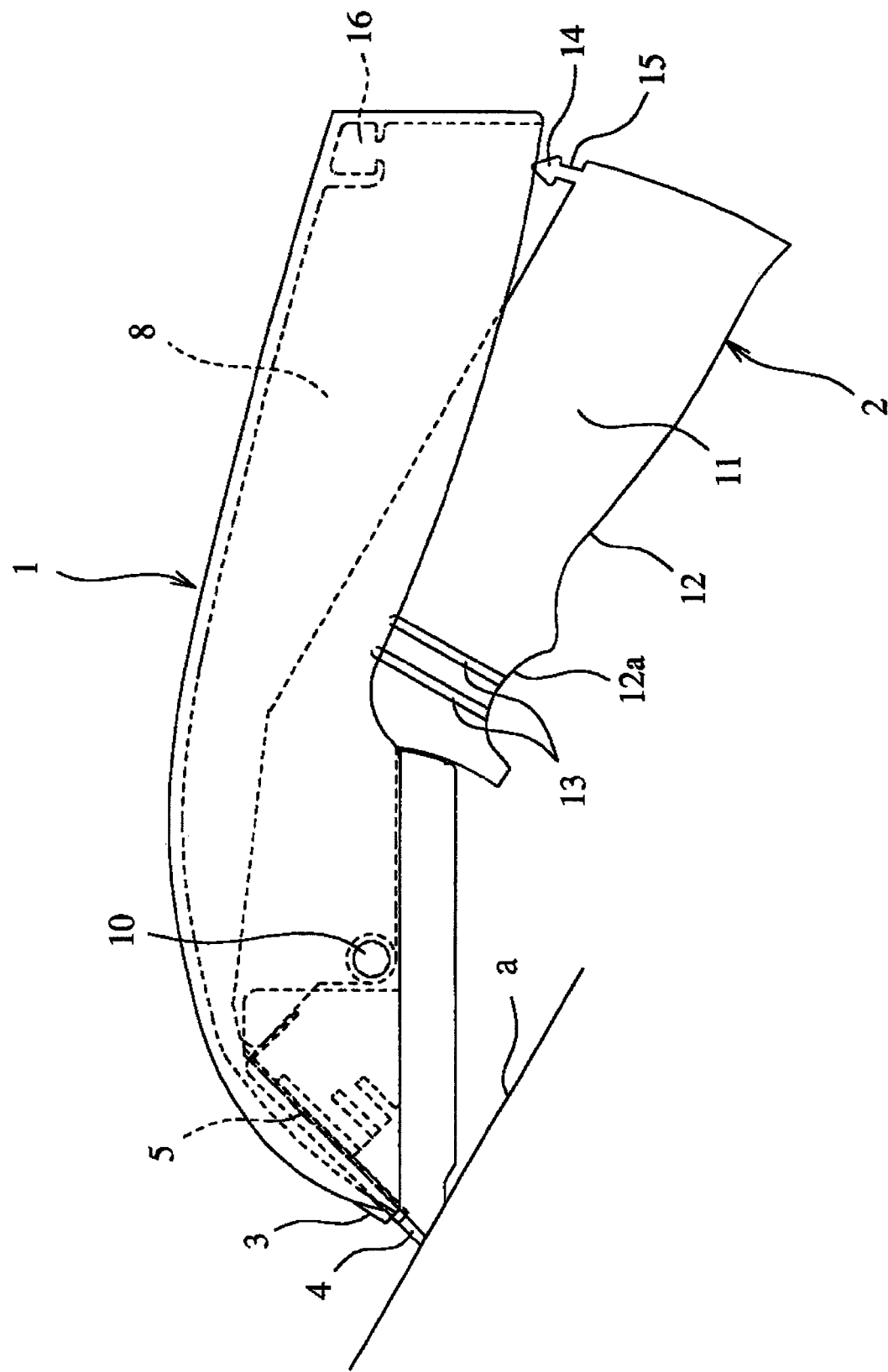
FIG. 1 is a side view illustrating a medical stapler according to a first exemplary embodiment of the invention.

S staple
1 stapler body
2 manipulating lever
3 head portion
8 accommodating portion
11 grip portion

BEST MODE FOR CARRYING OUT THE INVENTION

Hereinafter, exemplary embodiments of the invention are described with reference to the accompanying drawings. In each of the exemplary embodiments, a stapler body and a manipulating lever are the same as those of the other exemplary embodiments. Thus, each of the stapler body and the manipulating lever is designated with the same reference numeral as that designating an associated one of the stapler body and the manipulating lever of each of the other exemplary embodiments.

Additionally, the detail description of the stapler body and the manipulating lever is omitted in the descriptions of the exemplary embodiments other than a first exemplary embodiment.

First Exemplary Embodiment

FIG. 1 is a side view illustrating a medical stapler according to a first exemplary embodiment of the invention.

FIGS. 2(a) and 2(b) are a front view and a rear view of the medical stapler, respectively.

In the aforementioned figures, reference numeral 1 designates a stapler body. Reference numeral 2 designates a manipulating lever. Each of the stapler body 1 and the manipulating lever 2 is made of a synthetic resin. The stapler body 1 is longitudinally cross-sectionally substantially U-shaped. A head portion 3 for driving out medical staples is provided in a front portion of the stapler body 1. This head portion 3 is provided with a driving portion 4 for driving out medical staples. Several to dozens of medical staples S are loaded into the stapler body 1. The medical staples S are sequentially supplied by a feeding means (not shown) from a leading one of the staples S. A driver plate 5 is upwardly and downwardly slidably provided in an upper part of the driving portion 4 and is urged by a spring to be always placed at an upper position.

As illustrated in FIG. 2(a), the bottom portion of the driver plate 5 is shaped like an inverted "U". Projection pieces 6 are formed on both sides of the driver plate 5. Further, an anvil 7 is formed at an inwardly upper part of the driving portion 4. A central part of a leading staple S1 is placed on the anvil 7.

The manipulating lever 2 is such that a front portion thereof placed at the side of the head portion 3 is accommodated in an inner space (accommodating portion 8) of the stapler body 1. The manipulating lever 2 is attached turnably around a turning shaft 10 disposed at the side of the head portion 3 so that a grip portion 11 opposed to the head portion 3 is opened and closed. The grip portion 11 is normally urged by a spring or the like in an opening direction in which the grip portion 11 protrudes from the accommodating portion 8 and is spaced from the stapler body 1. A finger hook portion 12, around which four fingers from a forefinger to a little finger can be hooked, is formed on the grip portion 11 that protrudes from the accommodating portion 8 in this state.

Additionally, several thin portions 13 are formed near a forefinger hook portion 12a which is formed on the grip portion 11 of the manipulating lever 2. The thin portions 13 are formed so as not to be deformed by a grasping force which is applied the manipulating lever 2 in a normal suturing operation and has a magnitude of about 29.4 Newtons (N) to about 39.2 N (about 3 kgf to about 4 kgf). However, the thin portions 13 are formed so that when a large force, whose magnitude exceeds such a value, is applied thereto, the manipulating lever 2 is elongated and is elastically deformed in the vicinity of the thin portions 13. Further, a latch portion 15 having a latch jaw 14 is formed at an upper portion of the rear end of the manipulating lever 2 to upwardly protrude therefrom. A dovetail-groove-like latch receiving portion 16 corresponding to the latch portion 15 is formed at an upper part of the accommodating portion 8 of the stapler body 1 to be downwardly opened.

Figure 3:
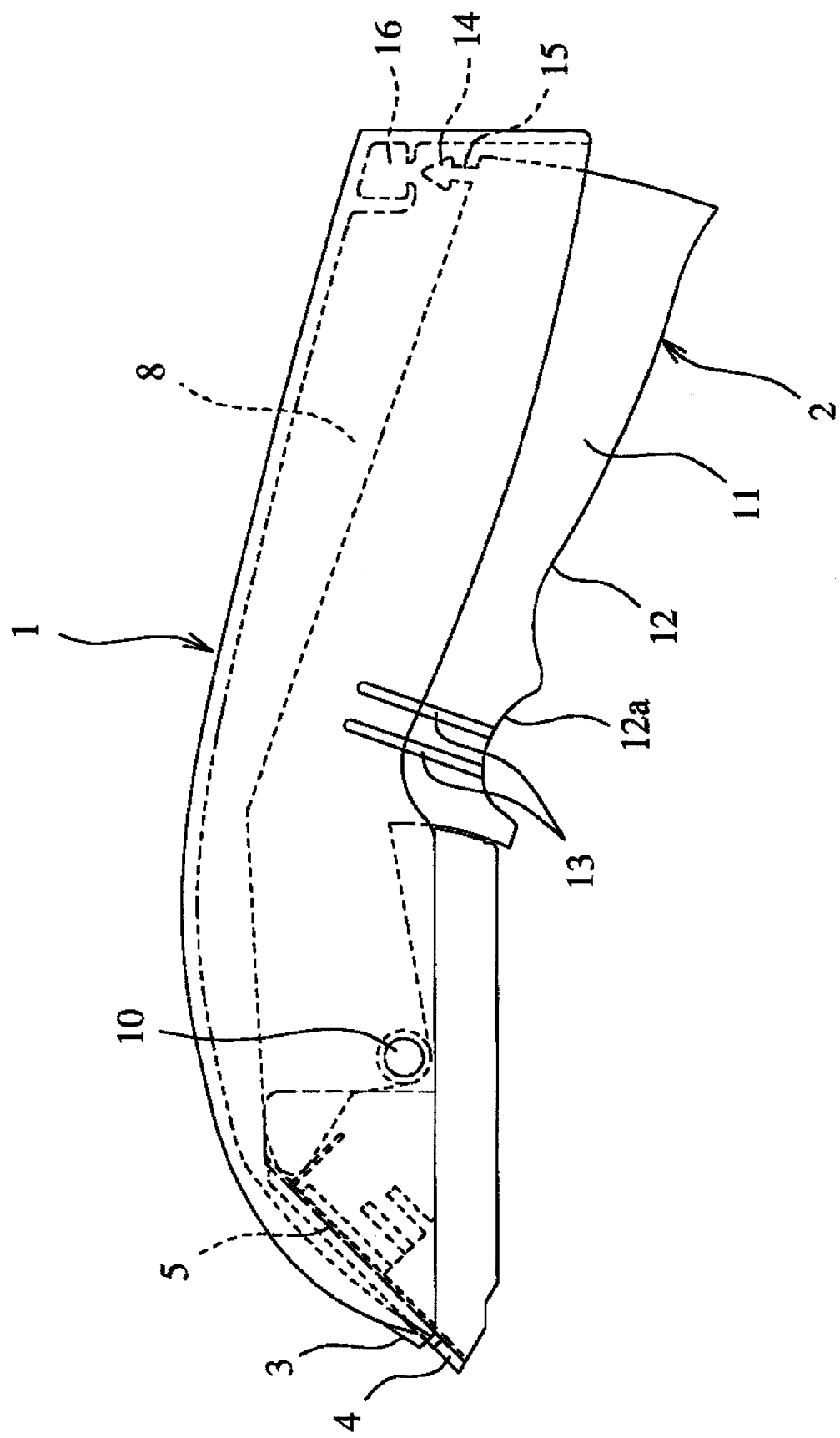
FIG. 3 is a side view illustrating the medical stapler at a normal operation.
Figure 4:
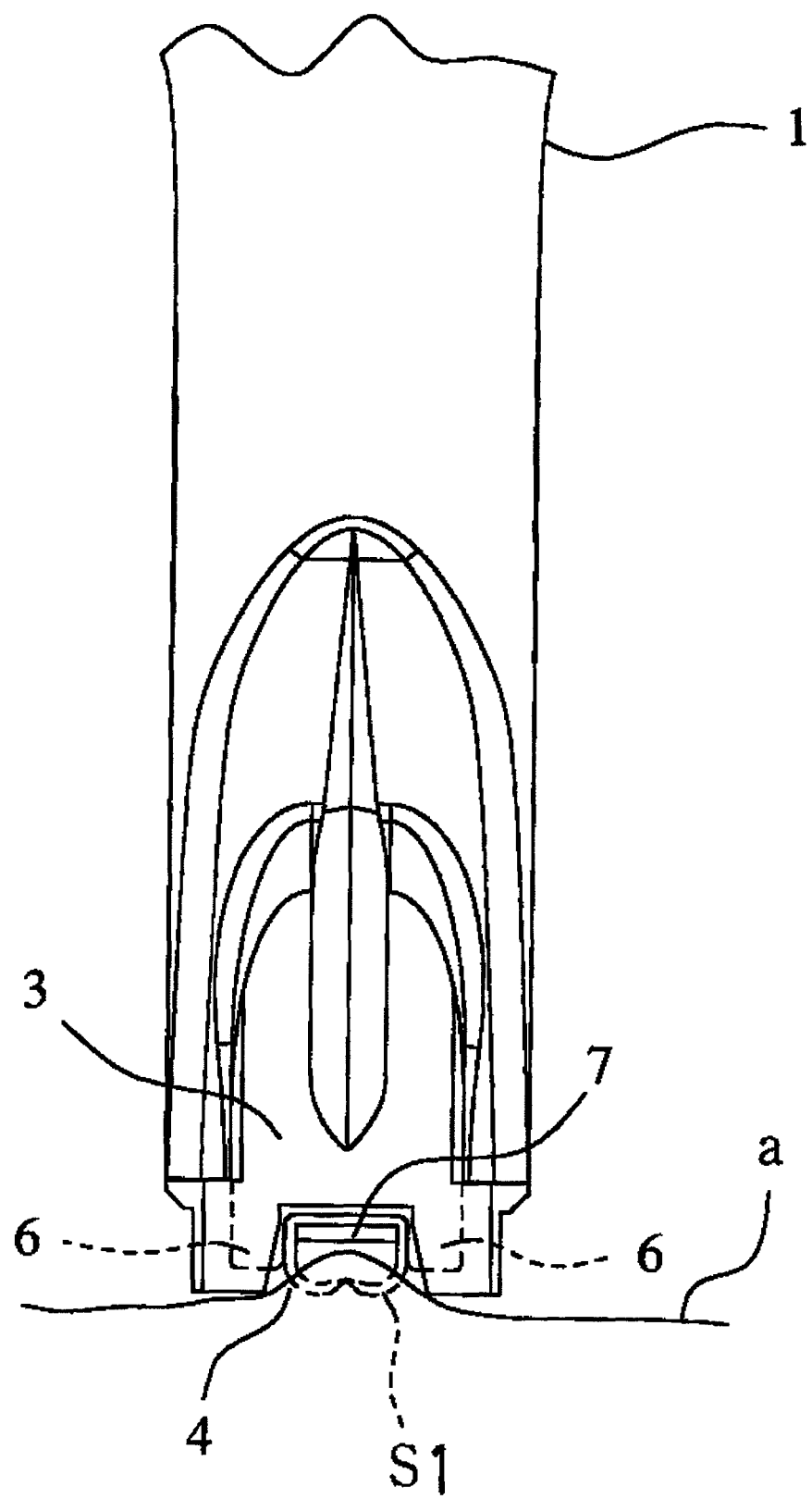
FIG. 4 is an enlarged front view of a staple, which illustrates a state thereof at driving-out thereof.

Next, an operating mode of the medical stapler is described below. A leading end of the head portion 3 is pushed onto skin "a" on both sides of a wound. Then, as illustrated in FIGS. 3 and 4, the manipulating lever 2 is turned in a closing direction in which the manipulating lever 2 is moved closer to the accommodating portion 8 to be accommodated therein. Thus, the staple S1 supplied to the driving portion 4 of the head portion 3 is pushed. At that time, the central part of the staple S1 is supported by the anvil 7. Therefore, the staple S1 cannot move downwardly any more. On the other hand, the projection pieces 6 formed on both sides of the driver plate 5 press both sides of the staple S1. Thus, only the tip end portions of the staple S1 are pushed down. Each of the tip end portions of the staple S1 is bent around an associated one of both ends of the anvil 7 so that the tip end portions thereof become close to each other. Subsequently, in the process of moving the manipulating lever 2 to a movement end, the tip end portions are inserted into the skin "a". Then, while the tip end portions at both ends of the staple S1 are inwardly bent, both sides of the wound are brought toward each other.

Thus, the wound is sutured.

The staple S1 is discharged from the head portion 3 by releasing the force applied to the manipulating lever 2 and restoring the grip portion 11 with an urging force in the opening direction in which the grip portion 11 protrudes from the accommodating portion 8 and is spaced from the stapler body 1. Thus, the suturing of the wound at one place is finished.

In the aforementioned operation, the thin portions 13 hardly change. Thus, the suturing of the entire wounds is completed by repeating the same operation.

Figure 5:
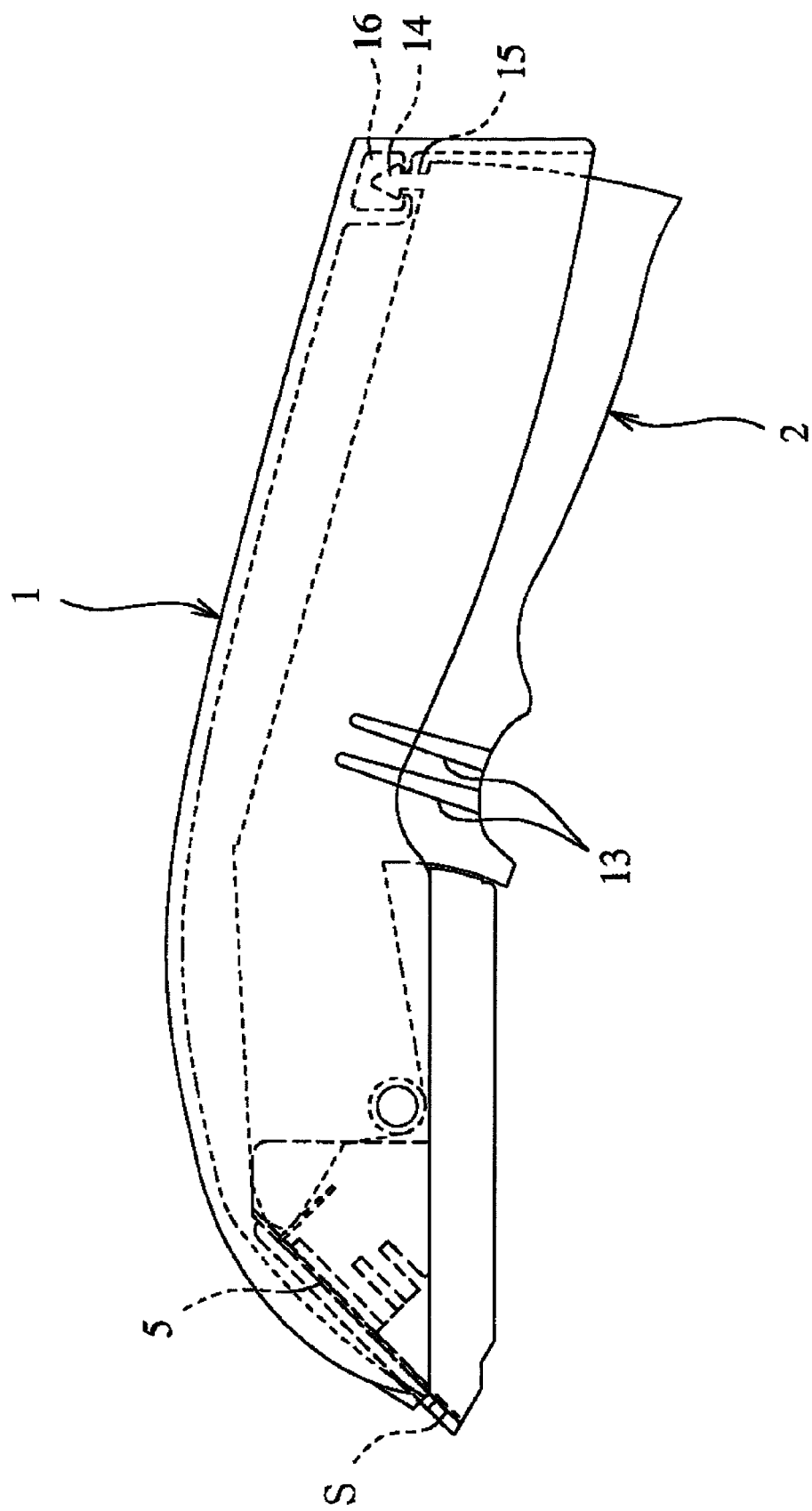
FIG. 5 is a side view of the medical stapler at disposal thereof.

Then, when the manipulating lever 2 is turned in the closing direction, in which the manipulating lever 2 is accommodated in the accommodating portion 8, upon completion of suturing of all wounds, a large force (i.e., a grasping force whose magnitude is about three times that of a normal force) is applied to the grip portion 11. Thus, the manipulating lever 2 is turned over a normal movable range, as illustrated in FIG. 5. Then, the thin portions 13 are extended, so that the entire manipulating lever 2 is elastically deformed. Consequently, the latch jaw 14 of the latch portion 15 provided on the manipulating lever 2 is latched to the latch receiving portion 16 that is provided in the stapler body 1. Accordingly, the manipulating lever 2 is accommodated in the accommodating portion 8 of the stapler body 1. Thus, the volume of the entire stapler is reduced. Hence, the volume of the stapler at the disposal thereof can be reduced. Thus, the present embodiment can contribute to reduction in the volume of medical wastes.

Finally, the manipulating lever 2 is latched in a state in which the manipulating lever 2 is turned in the closing direction in which the staple S1 is bent. The leading one of the staples S1 left in the head portion 3 is fixed in a state in which the tip end portions of the leading staple S1 is inwardly bent. Thus, the tip end portion of the staple S1 does not protrude from the stapler body 1. Consequently, even when an external force is applied to the manipulating lever 2 in the middle of processing of a garbage bag in which a medical stapler is discarded, there is no fear that the staple S1 pushed out of the stapler breaks through the garbage bag and is exposed. Accordingly, a disposal operation can safely be performed. In addition, a medical stapler can be discarded in a state, in which the remaining staples are left therein, without being disassembled. Consequently, there is no fear that the inside of an operating room is contaminated. Thus, all workers engaged in the disposal of medical wastes, which include not only employees of medical institutes but medical appliance waste disposers, can hygienically perform waste disposal.

Incidentally, slits can be formed as the thin portions 13 so that when a force whose magnitude is equal to or higher than a predetermined value is applied thereto, the slits are spread to elastically deform, and that the latch portion 15 of the manipulating lever 2 is latched in the latch receiving portion of the stapler body 1.

Further, the medical stapler can be constructed so that a dovetail-groove-like latch receiving portion is provided in the latch portion 15 of the manipulating lever 2, and that a latch jaw is provided in a corresponding part of the stapler body 1.

Second Exemplary Embodiment

Figure 6:
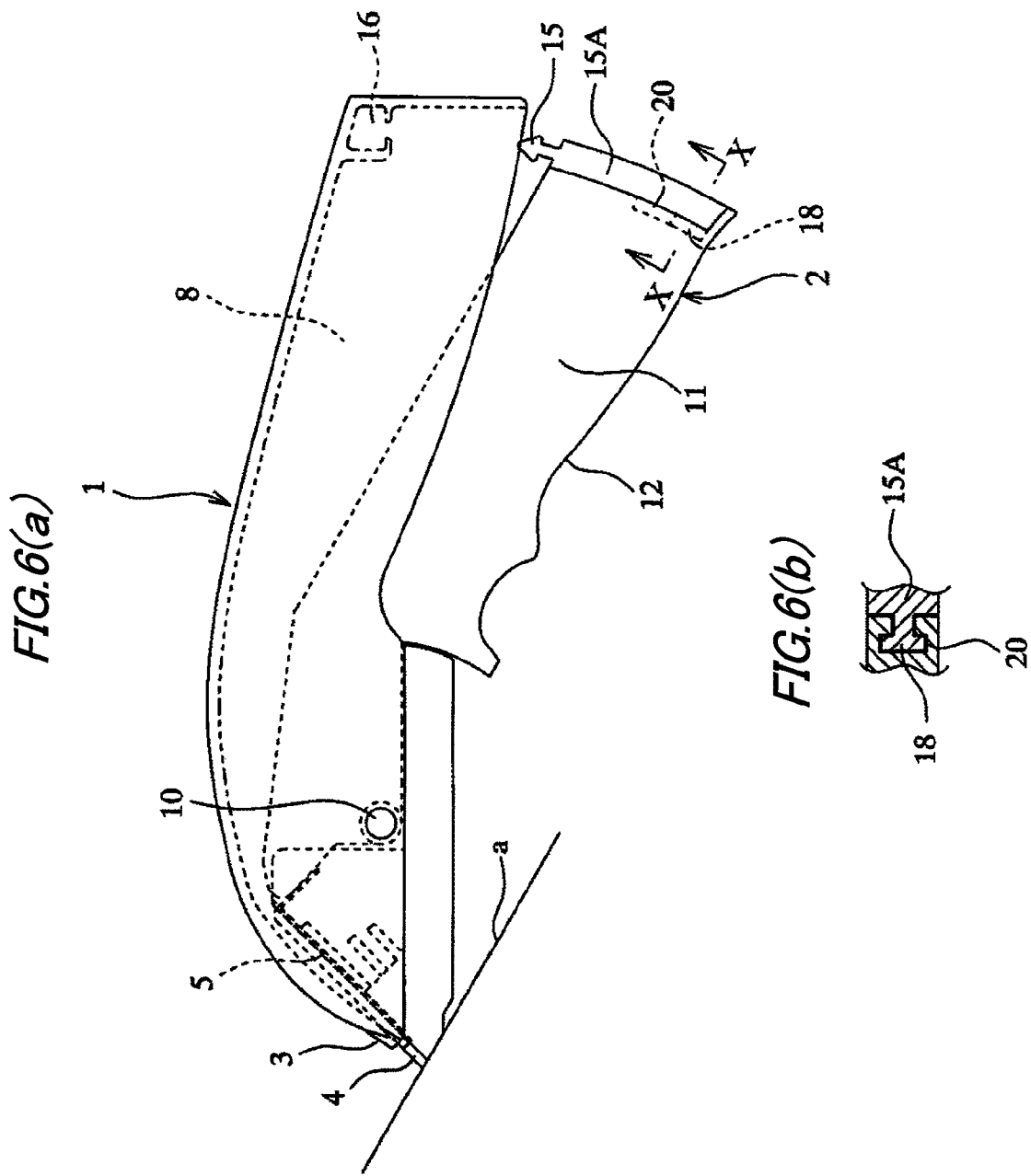
FIG. 6(a) is a side view of a stapler according to a second exemplary embodiment of the invention.
FIG. 6(b) is a cross-sectional view taken on line X-X illustrated in FIG. 6(a).

FIGS. 6(a) and 6(b) illustrate a second exemplary embodiment of the invention. A slide groove 20 is formed in an end part of a grip portion 11 of a manipulating lever 2. In the slide groove 20, a T-shaped engaging piece 18 of a latch member 15A is provided movably along a turning direction of the manipulating lever 2. A latch jaw (latch portion 15) is formed at the top end of the latch member 15A. On the other hand, a groove-like latch receiving portion 16 is formed in an upper part of an accommodating portion 8 of a stapler body 1 to be downwardly opened. The latch member 15A is set to be able to be operated to a standby position (position illustrated in FIGS. 6(a) and 7), at which the latch portion 15 is prevented from being latched in the latch receiving portion 16, and to a latchable position (position illustrated in FIG. 8), at which latching between the latch portion 15 and the latch receiving portion 16 is allowed.

Figure 7:
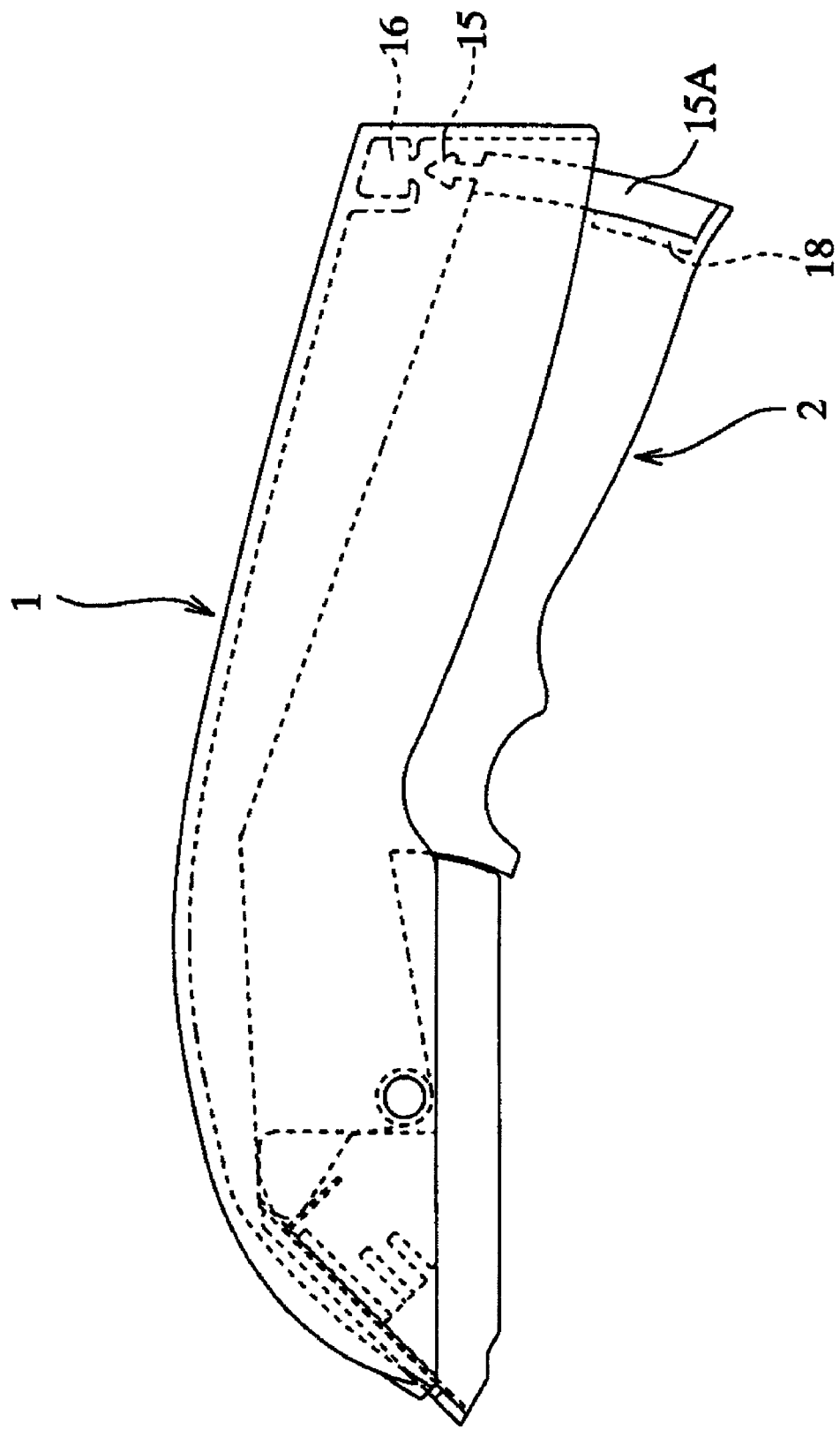
FIG. 7 is a side view of the medical stapler at a normal operation.
Figure 8:
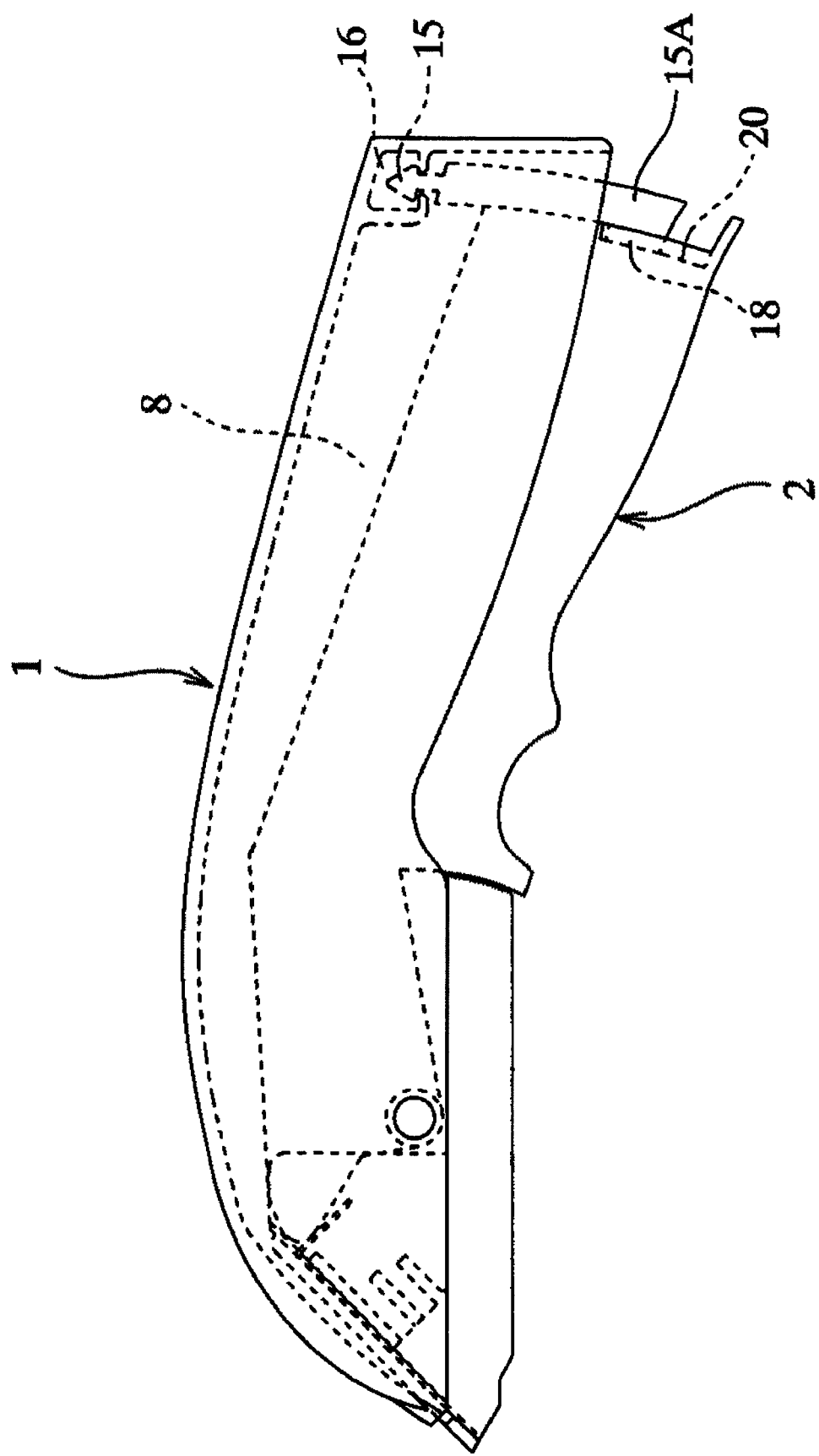
FIG. 8 is a side view of the medical stapler at disposal thereof.

In the aforementioned configuration, as illustrated in FIGS. 6(a) and 7, at normal suturing of a wound, the latch member 15A is placed at the standby position. Even when the manipulating lever 2 is turned in the closing direction, the latch portion 15 of the latch member 15A does not enter the latch receiving portion 16. Then, upon completion of suturing of all wounds, the manipulating lever 2 is turned in the closing direction in which the manipulating lever 2 is accommodated in the accommodating portion 8. Furthermore, the latch member 15A is operated to the latchable position illustrated in FIG. 8. Thus, the latch member 15A is latched to the latch receiving portion 16. Consequently, the manipulating lever 2 can be held in the closed state.

In this case, the closed state of the manipulating lever 2 can be held only by performing a one-touch simple operation on the latch member 15A. Thus, an operation of the manipulating lever 2 can easily be performed.

Incidentally, the latch member and the latch receiving portion can be formed mutually reversely. That is, as illustrated in FIGS. 9(a) and 9(b), a slide groove 20a is formed in the rear portion of the stapler body 1. A latch receiving member 16(a) engages with the slide groove 20a. The latch receiving portion 16 is formed at a lower end of the latch receiving member 16(a). A slip stopper is formed on the outer side of the latch receiving member 16(a). An engaging piece 18a engaging with the slide groove 20a is formed on the inner side of the latch receiving member 16(a). It is sufficient that the engaging piece 18a and the slide groove 20a are formed to have a relationship illustrated in FIG. 6(b). On the other hand, the latch portion 15 having the latch jaw 14 is formed at an upper part of the rear end of the manipulating lever 2 to protrude therefrom. The latch receiving member 16(a) is set to be able to be operated to the standby position, at which the latch receiving portion 16 prevents the latch portion 15 from being latched to the latch jaw 14, and the latchable position at which the latching between the latch portion 15 and the latch receiving portion 16 is allowed.

With the aforementioned configuration, at normal suturing of a wound, the latch receiving member 16(a) is held at the standby position at the top end thereof. Even when the manipulating lever 2 is turned in the closing direction, the latch jaw 14 of the latch portion 15 does not enter the latch receiving portion 16. Further, upon completion of suturing of all wounds, the latch receiving member 16(a) is downwardly slid to the latchable position. Then, the manipulating lever 2 is turned in the closing direction, in which the manipulating lever 2 is accommodated into the accommodating portion 8, to latch the latch jaw 14 of the latch portion 15 to the latch receiving portion 16 of the latch receiving member 16(a). Consequently, the manipulating lever 2 can be held in the closed state.

Figure 10A:
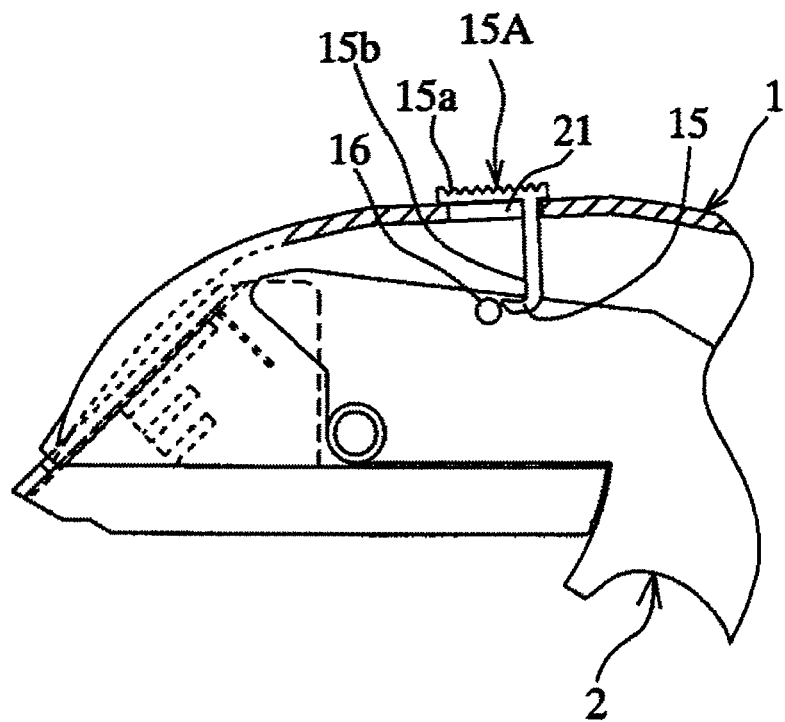
FIG. 10(a) is a side view of a part of a medical stapler according to still another example of the second exemplary embodiment.

Additionally, the direction of operating the latch member and the latch receiving portion is not limited to the aforementioned upward and downward opening and closing directions. For example, as illustrated in FIG. 10(a), the latch receiving portion 16 can be formed at an upper portion of the manipulating lever 2. Further, the stapler body 1 can be provided with the latch member 15A so that the latch member 15A slides in the forward and rearward directions perpendicular to the opening and closing directions. The latch receiving portion 16 is formed to axially protrude from both sides of the front portion of the manipulating lever 2. On the other hand, the latch member 15A has leg portions 15b that are pendent downwardly from a top surface plate 15a. The latch portion 15 latchable to the latch receiving portion 16 is formed at the bottom of each of the leg portions 15b to frontwardly bend.

Figure 10B:
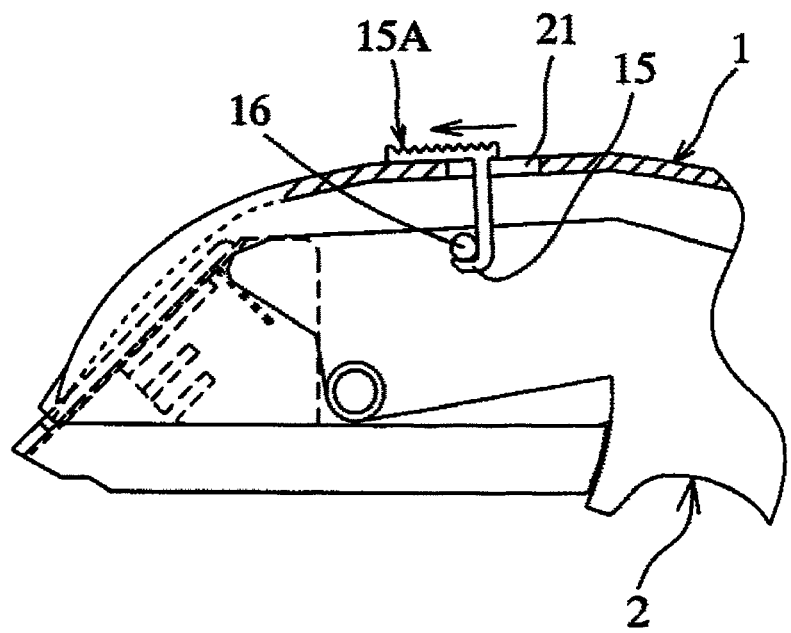
FIG. 10(b) is a side view of a part of the medical stapler illustrated in FIG. 10(a), which is in a latched state.

The latch portion 15 is provided slidably in the slide groove 21 formed in the top portion of the stapler body. The top surface plate 15a of the latch member 15A is provided slidably along the outer surface of the stapler body 1. The latch member 15A is set to be positionable at the standby position (position illustrated in FIG. 10(a)), at which latching between the latch portion 15 and the latch receiving portion 16 is prevented, and at the latchable position (position illustrated in FIG. 10(b)) at which the latching between the latch portion 15 and the latch receiving portion 16 is allowed.

With the aforementioned configuration, at normal suturing of a wound, the latch member 15A is retreated to a backward standby position at which the latch member 15A cannot be latched to the latch receiving portion 16. Further, when the suturing of the wound is finished, a closing operation is performed by grasping the manipulating lever 2. Then, the latch member 15A of the stapler body 1 is frontwardly moved to the latchable position. Consequently, the latch portion 15 is latched to the latch receiving portion 16 of the manipulating lever 2.

Thus, the manipulating lever 2 is held in the closed state.

Incidentally, it is sufficient that the latch receiving portion can be latched to the latch portion. The latch receiving portion can be formed like a hook, instead of being formed like a shaft.

Further, in this case, the medical stapler can be configured to that the latch member is slidably provided on the manipulating lever and that the latch receiving portion is provided in the stapler body.

Next, referring to FIGS. 11(a), 11(b) and 11(c), there is illustrated another example of the embodiment. A latch receiving member 16(a) is upwardly and downwardly slidably provided in a rear surface portion of the stapler body 1. The latch receiving member 16(a) is an elongated member. Similarly to the example illustrated in FIG. 6(b), an engaging projection piece 18b slidably engaging with a slide groove 20b formed in the rear surface portion of the stapler body 1 to extend upwardly and downwardly is formed at the top of the latch receiving member 16(a). A first holding projection portion 70 is formed at a middle portion of the latch receiving member 16(a). A groove-like latch receiving portion 16 is formed in a lower part of the first holding projection portion 70. A second holding projection portion 71 is formed at a lower part of the rear surface portion of the stapler body 1. The first holding projection portion 70 and the second holding projection portion 71 constitute a holding means for holding the latch portion 15 at a predetermined position. The second holding projection portion is formed engageably with an inclined surface of the upper and lower parts of the first holding projection portion.

On the other hand, the tongue-like latch portion 15 is formed at the rear end portion of the manipulating lever 2 engageably with the latch receiving portion 16 to backwardly project therefrom.

In the aforementioned configuration, at suturing of the wound, the second holding projection portion 71 is engaged with a lower part surface of the first holding projection portion 70 of the latch receiving member 16(*a*). Thus, the latch receiving member 16(*a*) is held at the upward standby position illustrated in FIG. 11(*a*). Even when the manipulating lever 2 is operated in the closing direction at the standby position, the latch portion 15 is not latched to the latch receiving portion 16 of the latch receiving member 16(*a*). Thus, the manipulating lever 2 can freely perform opening and closing operations. Consequently, a suturing operation can be performed.

Upon completion of suturing of the wound, the manipulating lever 2 is grasped to thereby put the manipulating lever 2 into a closed state. Then, the latch receiving member 16(*a*) is moved to the downward latchable position illustrated in FIG. 11(*c*). When the latch receiving member 16(*a*) is downwardly slid, the first holding projection portion 70 overrides the second holding projection portion 71. Thus, the latch receiving member 16(*a*) is backwardly pushed out, so that the latch receiving portion 16 is retreated to the rear of the latch portion 15.

Then, after the first holding projection portion 70 overrides the second holding projection portion 71, the latch receiving portion 16 of the latch receiving member 16(*a*) frontwardly moves to be latched to the latch portion 15. In addition, the second holding projection portion 71 engages with the upper part surface of the first holding projection portion 70. Thus, the latch receiving member 16(*a*) is held at the downward latchable position. Additionally, the manipulating lever 2 is held in the closed state.

Next, referring to FIGS. 12(*a*), 12(*b*), and 12(*c*), there is illustrated still another example of the present embodiment.

The latch portion 15 is formed at the rear end side of the manipulating lever 2. On the other hand, the latch receiving portion 16 constituted by a latch hole, to which the latch portion 15 can be latched, is formed in the rear end side of the stapler body 1.

That is, the latch portion 15 is formed on the top surface of the rear part of the manipulating lever 2 to upwardly protrude therefrom. The latch jaw 14 is formed at a leading end part of the latch portion 15.

An inverted-U-shaped cutout 44 is formed in an outer surface of a rear surface portion 43 of the stapler body 1. The latch receiving member 16(*a*) is swingably provided in the cutout 44. That is, the latch receiving member 16(*a*) includes a pressing portion (operating portion) 45 and a latch piece portion 47.

The pressing portion 45 is formed to be able to swing around a base part 46 thereof. The latch piece portion 47 is formed on the rear side of the pressing portion 45 to extend to the inner side of the stapler body 1. The latch receiving portion (latch hole) 16 is formed in the latch piece portion 47 to penetrate therethrough. Incidentally, a deflection preventing rib 48 is formed on an upper part of the latch piece portion 47 at the rear side of the pressing portion 45. Further, a lower part of the latch piece portion 47 is formed integrally with a triangular rib 49.

Figure 13:
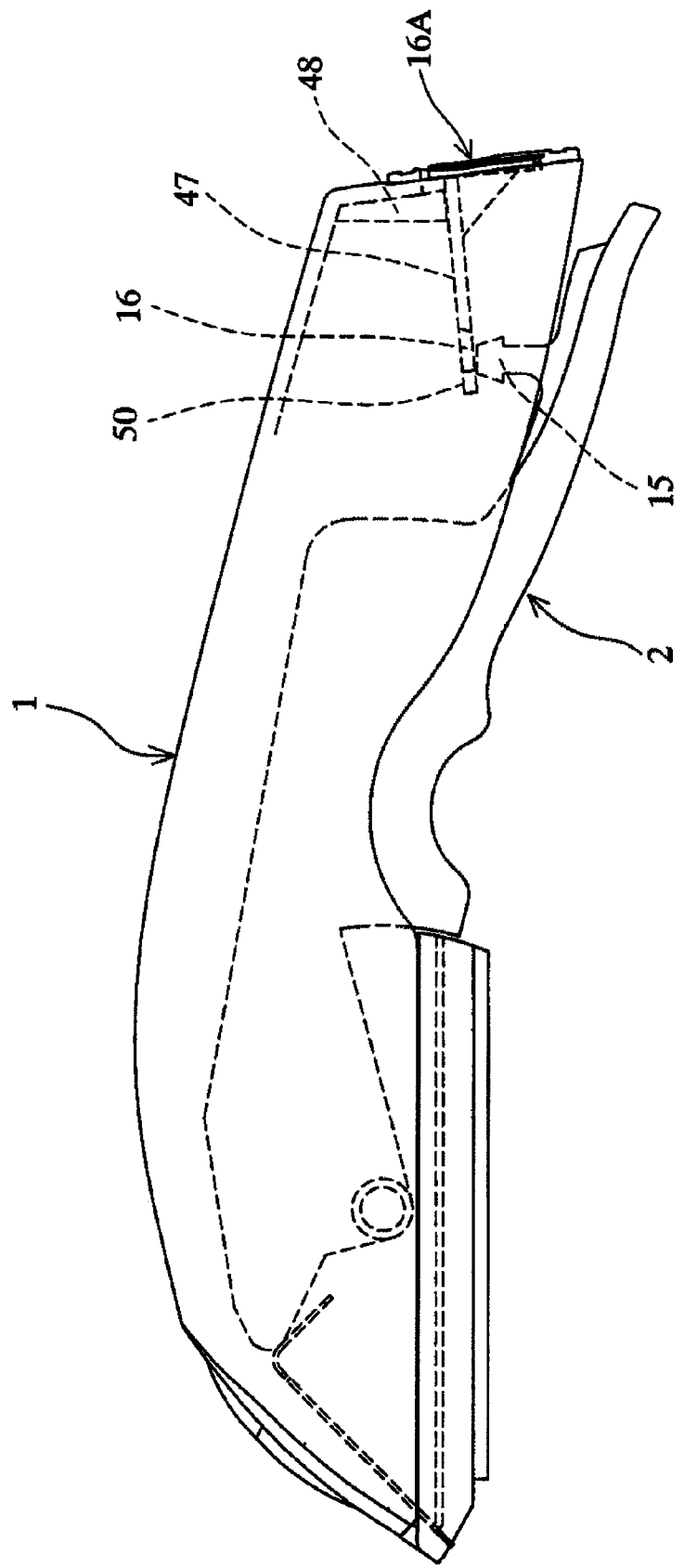
FIG. 13 is a side view illustrating a normal operating state of the medical stapler illustrated in FIG. 12(a).

Meanwhile, the stapler body 1 is formed of a synthetic resin by molding. Therefore, when the pressing portion 45 is pushed into the stapler body 1, the base part 46 of the cutout 44 is elastically deformed and is deflected so as to swing. Thus, the latch piece portion 47 is turned due to this swing motion, so that the position of the latch receiving portion 16 is changed. Thus, when the latch portion 15 is upwardly moved by operating the manipulating lever 2 in the closing direction without applying a force to the pressing portion 45, the leading end of the latch portion 15 abuts against a front edge portion 50 of the latch receiving portion 16 (see FIG. 13).

Then, a position, at which the latch receiving portion 16 is prevented from entering the inside of the latch receiving portion 16, is set as the standby position (position illustrated in FIGS. 12(*a*) to 13) of the latch receiving member 16(*a*). Further, when the pressing portion 45 is pushed to the front from the rear thereof, the latch receiving portion 16 is elastically deformed and moves together with the latch piece portion 47. At that time, the manipulating lever 2 is operated in the closing direction in which the manipulating lever 2 is accommodated in the accommodating portion 8. Thus, the latch portion 15 having been upwardly moved is permitted to enter the latch receiving portion 16. Then, a position, at which the latching between the latch portion 15 and the latch receiving portion 16 is allowed, is set as the latchable position (position illustrated in FIGS. 14 and 15) of the latch receiving member 16(*a*). Incidentally, when the pressing portion 45 is excessively pushed thereinto, there is a fear that a bent part (base part 46) is damaged. However, when the pressing portion 45 is excessively pushed thereinto, the top edge of the pressing portion 45 engages with the rear end of the deflection preventing rib 48. Thus, the medical stapler is adapted so that the pressing portion 45 cannot be pushed any more. Accordingly, the positioning of the latchable position is achieved.

Thus, the latch receiving portion 16 is provided to be movable between the standby position and the latchable position according to whether the pressing portion 45 is pushed thereinto.

With the aforementioned configuration, the pressing portion 45 is not pressed at normal suturing of a wound. A suturing operation is performed in a state in which the latch receiving portion 16 is placed at the standby position illustrated in FIGS. 12(*b*) and 13. In this case, even when the manipulating lever 2 is operated any more after the manipulating lever 2 is operated in the closing direction (i.e., a staple driving direction), the leading end of the latch portion 15 only abuts against the front edge portion 50 of the latch receiving portion 16 of the latch piece portion 47. However, the leading end of the latch portion 15 cannot enter the inside of the latch receiving portion 16. Because the latch portion 15 cannot be latched to the latch receiving portion 16, the manipulating lever 2 is operated in a downward opening direction when a force applied to the manipulating lever 2 is released after a closing operation is performed. Incidentally, in a case where the manipulating lever 2 is strongly grasped, the latch piece portion 47 is pressed up and is deflected. Thus, there is a fear that the latch portion 15 enters the latch receiving portion 16. However, because the deflection preventing rib 48 is formed at an upper part of the latch piece portion 47, the latch piece portion 47 is not easily deflected even when the latch piece portion 47 is pressed up. Additionally, when the manipulating lever 2 is strongly grasped, an operation of pushing up the latch portion 2 is suppressed by the latch piece portion 47.

Figure 14:
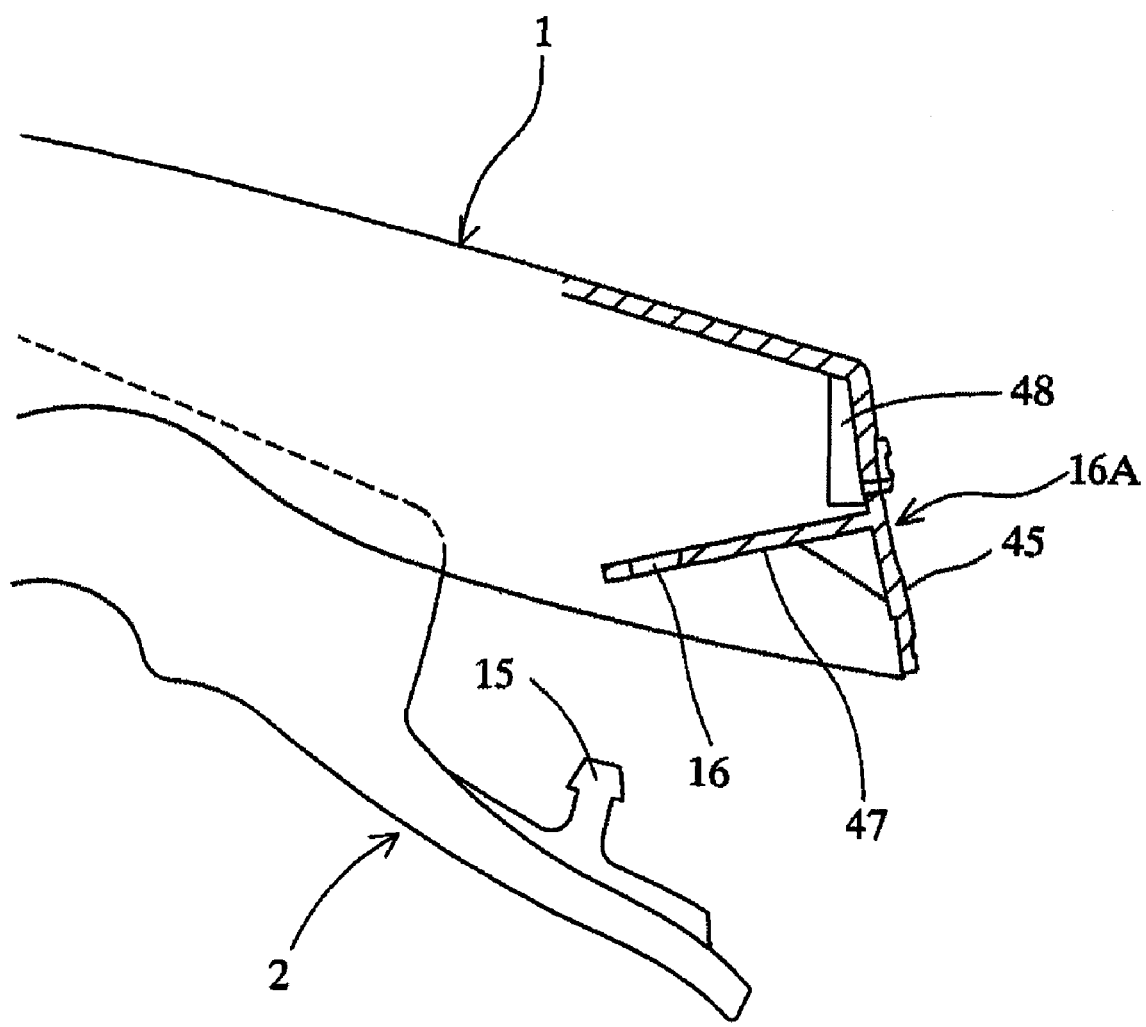
FIG. 14 is an enlarged cross-sectional view of a part of the medical stapler illustrated in FIG. 12(a).
Figure 15:
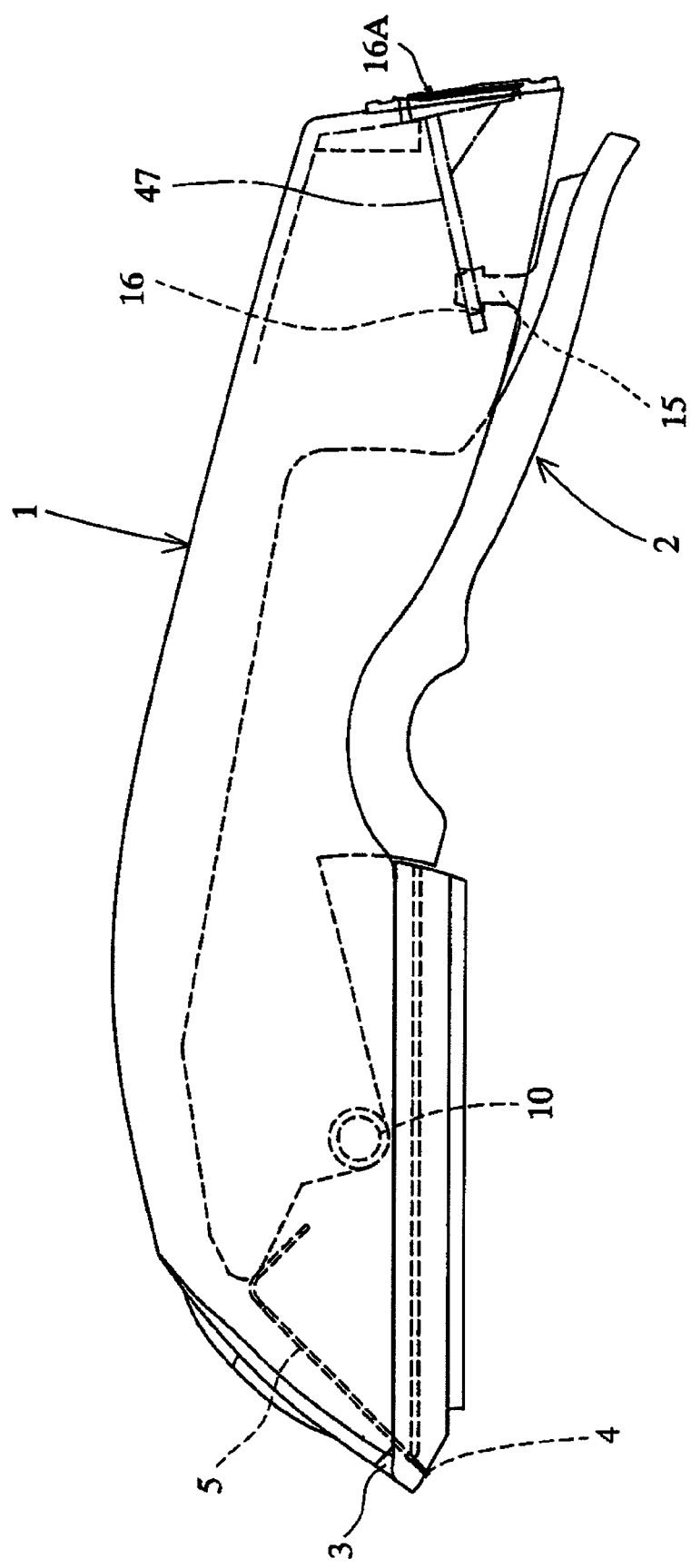
FIG. 15 is a side view illustrating an operating state of the medical stapler illustrated in FIG. 12(a), in which the medical stapler is discarded.
Figure 16:
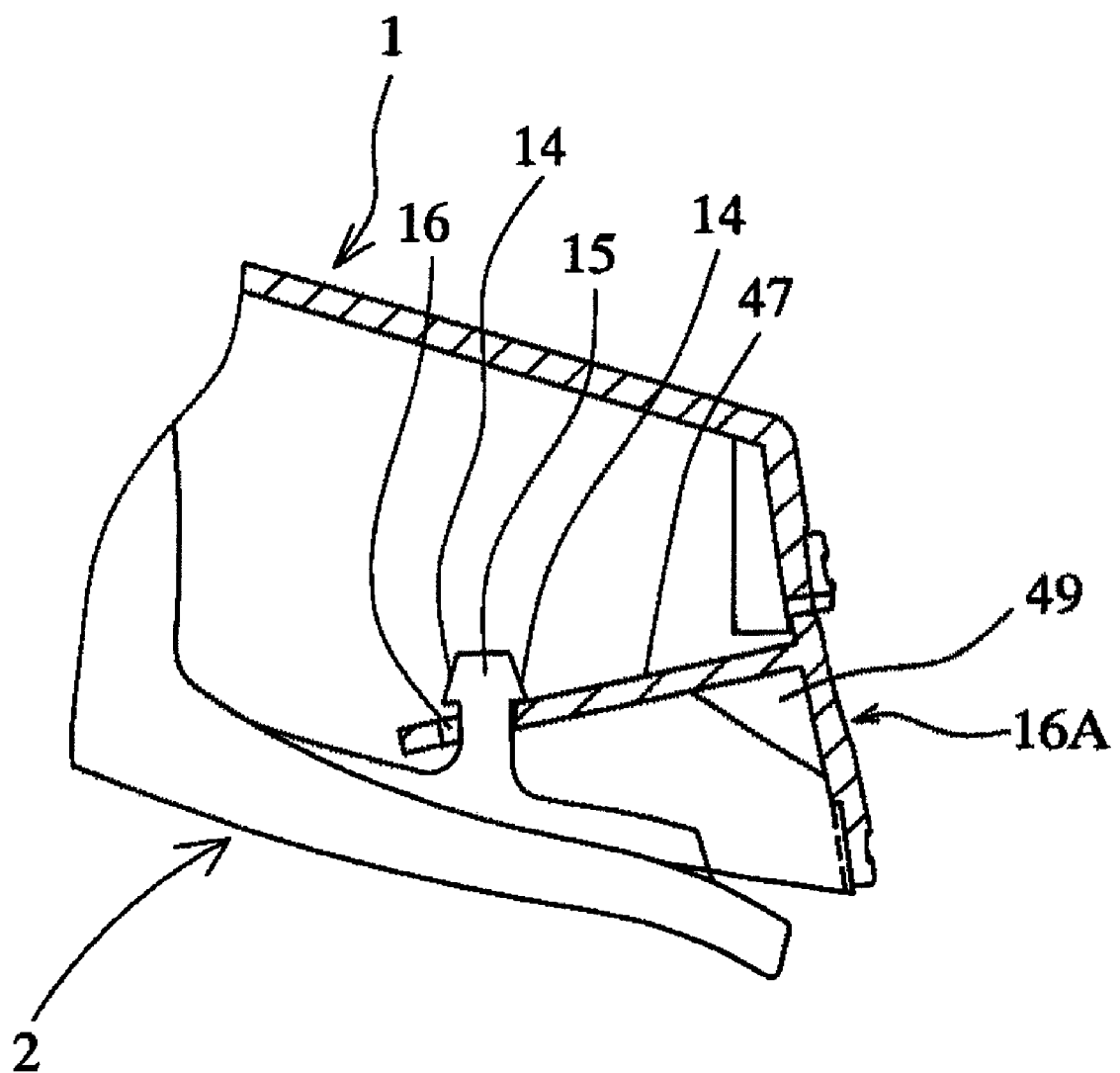
FIG. 16 is a side view illustrating a latched state of a manipulating lever of the medical stapler illustrated in FIG. 12(a).

On the other hand, when the medical stapler is discarded upon completion of performing the operation of suturing of the wound, the pressing portion 45 is pressed thereinto by a finger, as illustrated in FIG. 14. Thus, the latch portion 15 is moved to the latchable position. When the manipulating lever 2 is grasped and is turned in the closing direction in this state, as illustrated in FIG. 15, the latch portion 15 enters the latch receiving portion 16. Then, the latch portion 15 penetrates therethrough, as illustrated in FIG. 16. Thus, the latch jaw 14 is latched to the latch receiving portion 16. Consequently, even when the force applied to each of the pressing portion 45 and the manipulating lever 2 is released, a latched state is held. Neither the pressing portion 45 nor the manipulating lever 2 returns to an initial position. Thus, the medical stapler is held in the closed state. Incidentally, the manipulating lever 2 is downwardly urged by a spring. Thus, the latch piece portion 47 also undergoes a force so as to deflect downwardly. However, the flexural deformation of the latch piece portion 47 is prevented by the triangular rib 49. Thus, the closed state is assured for a long time.

Accordingly, even when the force applied to the manipulating lever 2 is released, the latched state is held. The manipulating lever 2 is not returned to the initial position. The medical stapler is held in the closed state. Thus, the medical stapler can be discarded in a safe state. Further, unless the pressing portion 45 is pressed, the latch receiving portion 16 is not operated to the latchable position. Consequently, there is no fear that the manipulating lever 2 is erroneously held in the closed state.

Incidentally, the configurations of the latch portion and the latch receiving portion are not limited to the aforementioned ones. For example, it is not necessarily required that the pressing portion 45 and the latch piece portion 47 are formed integrally with each other. Moreover, the configuration of the medical stapler is not limited to that in which the latch receiving portion 16 at the side of the stapler body 1 is operated. For example, the structure of the medical stapler can be adapted so that the latch portion at the side of the manipulating lever 2 is operated to the standby position and the latchable position. Furthermore, the configuration of the latch portion 15 and the latch receiving portion 16 can be adapted so that the downward latch portion is formed at the side of the latch piece portion 47, and that the latch receiving portion latchable to the aforementioned latch portion 15 is formed at the side of the manipulating lever 2, reversely to the aforementioned structure.

Further, although the aforementioned embodiment is such that after the pressing portion 45 is pressed by a finger, the manipulating lever 2 is grasped and is turned in the closing direction to latch the latch portion 15 to the latch jaw 14, the latching between the latch portion 15 and the latch jaw 14 can be performed by performing an operation of pressing the pressing portion 45 after the manipulating lever 2 is grasped.

In the former case, the latching between the latch portion and the latch receiving portion is allowed by turning the manipulating lever 2 in the closing direction after the pressing portion 45 is operated. Thus, unless the pressing portion 45 is operated, the latching between the latch portion and the latch receiving portion is not performed even when the manipulating lever 2 is put into the closed state. Consequently, there is no fear that the manipulating lever 2 is erroneously held in the closed state. In the latter case, the latching between the latch portion and the latch receiving portion is allowed by operating the pressing portion 45 after the manipulating lever is turned in the closing direction. Thus, unless the pressing portion 45 is operated after the manipulating lever is grasped, the latching between the latch portion and the latch receiving portion is not performed. Consequently, there is no fear that the manipulating lever 2 is held in the closed state. In addition, because the operating portion is operated after an operation of grasping the manipulating lever 2, a user can successively transit the operation of grasping the manipulating lever to a disposal operation without feeling odd.

Figure 18:
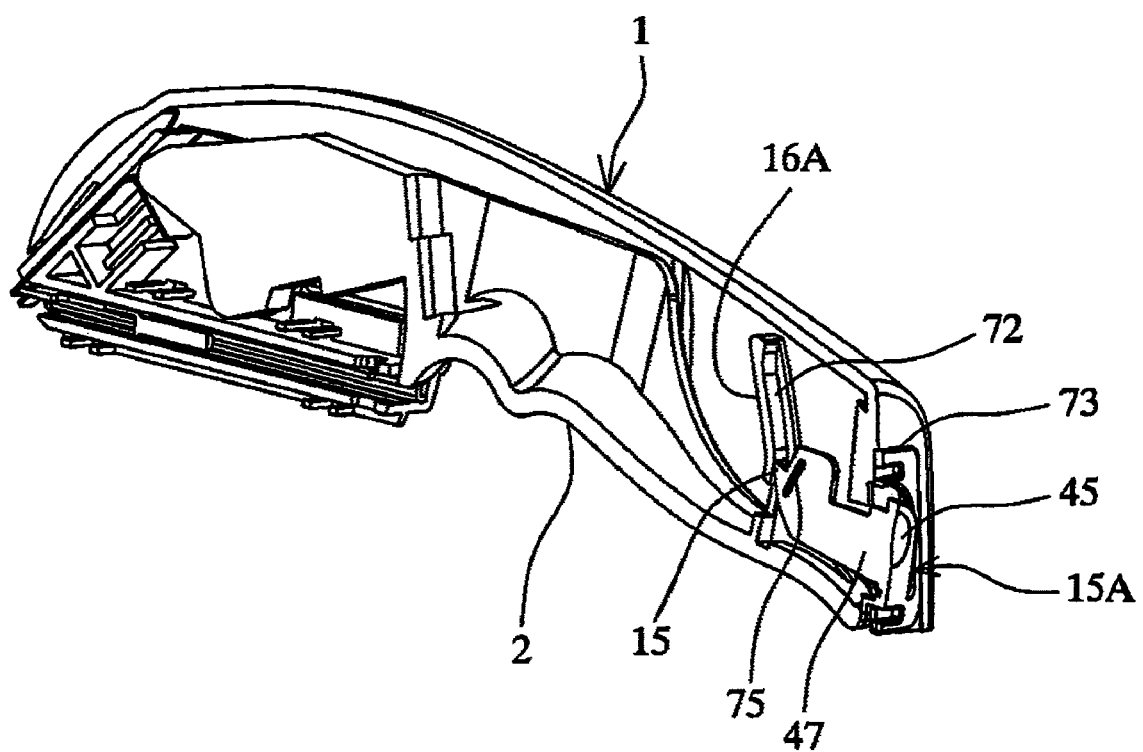
FIG. 18 is a perspective view illustrating a state of the medical stapler illustrated in FIG. 17(a) longitudinally cut into half in a condition in which the manipulating lever is operated in a closing direction.

Furthermore, reversely to the procedure according to the aforementioned embodiment, the procedure can be changed so that the latch jaw (or latch portion) is formed on the aforementioned latch piece portion, and that then, the latch receiving portion is formed in the latch portion. That is, as illustrated in FIGS. 17(a) and 17(b), the latch receiving member 16(a) upwardly protruding is formed on the top surface of the rear portion of the manipulating lever 2. Then, the latch receiving portion 16 is formed in the latch receiving member 16(a). A part of the latch receiving member 16(a), which is upper than the latch receiving portion 16, is frontwardly bent. Moreover, a rear surface portion 72 of the latch receiving member 16(a) is formed like a groove, as illustrated in FIG. 18. On the other hand, an opening portion 73 is formed in the rear surface portion 43 of the stapler body 1. Further, a frame plate 74 is latched and fixed to the peripheral part of the opening portion 73. The inverted-U-shaped cutout 44 is formed in the frame plate 74. The latch member 15A is swingably provided at the inner side of the cutout 44. The latch member 15A includes the pressing portion (operating portion) 45 and the latch piece portion 47. The pressing portion (operating portion) 45 is adapted to be able to swing around the base part 46. The latch piece portion 47 is formed on the rear side of the pressing portion 45 to extend to the inner side of the stapler body 1. The latch portion 15 is formed at an end of the latch piece portion 47 via a slit 75. The latch portion 15 is provided thereon to be brought into sliding contact with the rear surface portion 72. Additionally, during the latch member swings, the top part of the pressing portion 45 engages with the edge part of the opening portion 73 and restrains the latch member from swinging any more.

In this case, when a user operates the manipulating lever 2 in the closing direction without applying a force to the pressing portion 45, the rear surface portion 72 and the latch portion 15 are in sliding contact with each other. Thus, the base part 46 is elastically deformed due to the bend of the latch receiving member 16(a). A position, to which the pressing portion 45 is backwardly turned to prevent an end of the latch receiving member 16(a) from being latched to the latch portion 15, is set as the standby position (position illustrated in FIGS. 17(a), 18 and 19) of the latch member 15A. Further, when the pressing portion 45 is pushed from the rear to the front thereof, the base part 46 is elastically deformed, so that the latch portion 15 downwardly moves together with the latch piece portion 47 to a lower position. This position is set as the latchable position (position illustrated in FIG. 20), at which the latching between the latch member 15A and the latch receiving portion 16 is allowed by operating the manipulating lever 2 in the closing direction.

Figure 19:
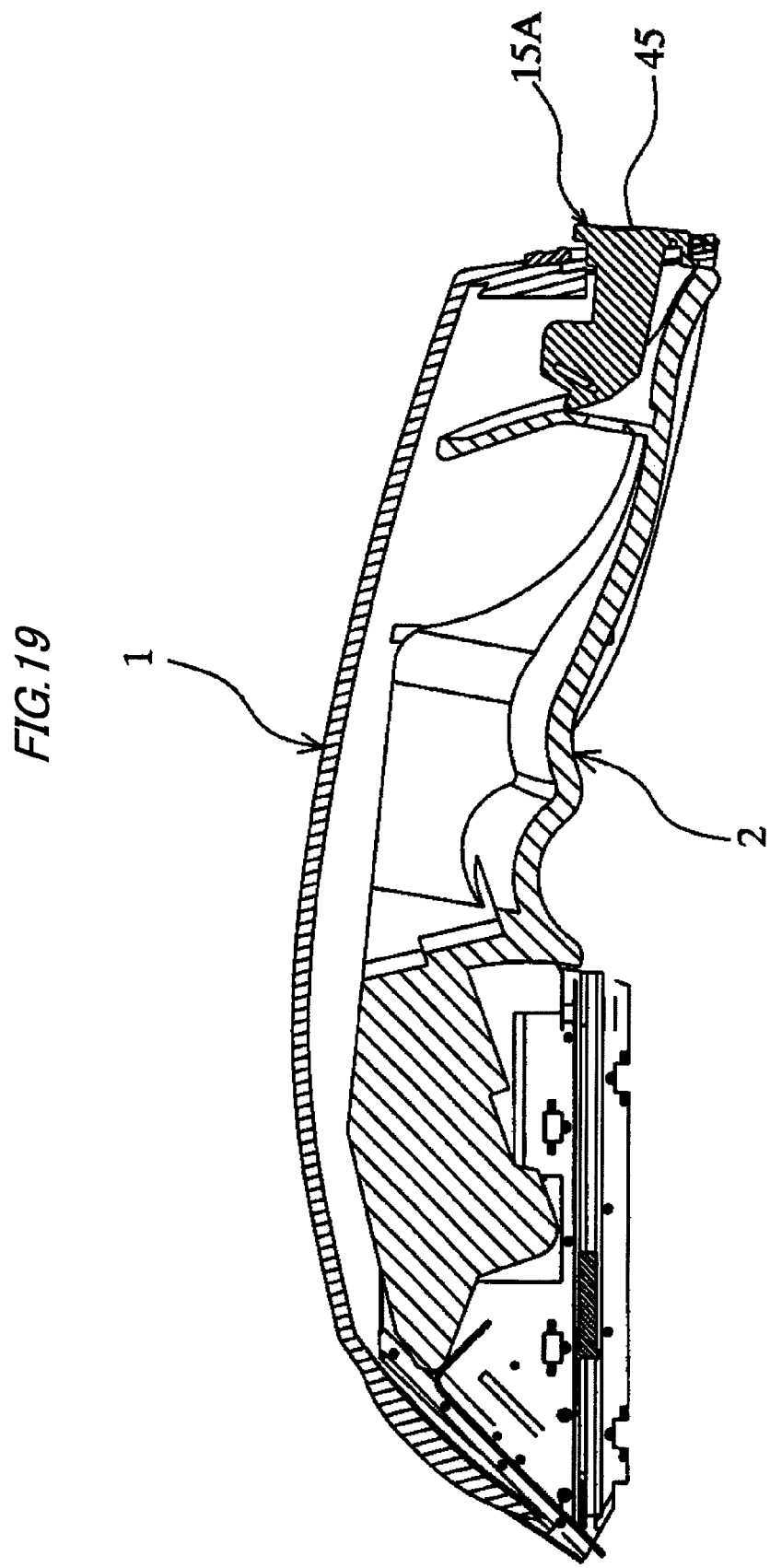
FIG. 19 is a cross-sectional view illustrating a state in which the manipulating lever is closed in a standby position of the medical stapler illustrated in FIG. 17(a).

In the aforementioned configuration, a normal suturing operation is performed in a state, in which the latch portion 15 is placed at the standby position illustrated in FIGS. 17(a), 18, and 19, without pressing the pressing portion 45. In this case, it is sufficient to drive staples by grasping the manipulating lever 2 and then operating the manipulating lever 2 in the closing direction (staple driving direction). In the middle of a turn of the manipulating lever 2 in the closing direction, the latch portion 15 of the latch piece portion 47 is guided and slides along the groove-like rear surface portion 72 of the latch receiving member 16(a) and is pushed out backwardly to be returned to the standby position. As the pressing portion 45 backwardly swings around the base part 46 thereof, the latch piece portion 47 and the latch portion 15 of the latch receiving member 16(a) are upwardly turned.

Thus, the latch portion 15 cannot be latched to the latch receiving portion 16 of the latch receiving member 16(a). Upon completion of performing a closing operation, when a force applied to the manipulating lever 2 is released, the manipulating lever 2 is operated in a downward opening direction.

Figure 20:
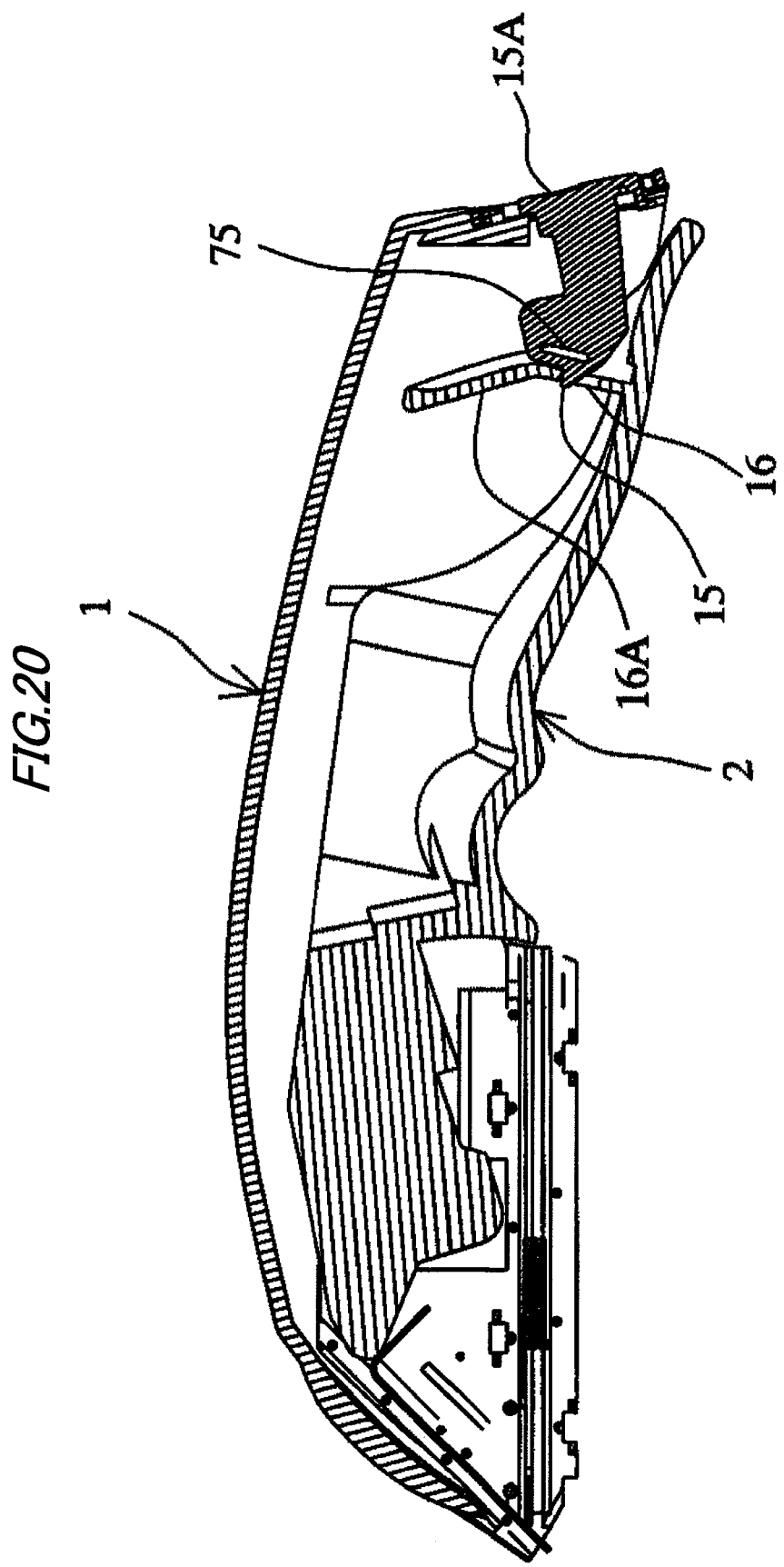
FIG. 20 is a cross-sectional view illustrating a state of the medical stapler illustrated in FIG. 17(a) at disposal thereof.

On the other hand, when the medical stapler is discarded upon completion of performing the suturing operation, the latch member 15A is moved to the latchable position by pressing the pressing portion 45 with a finger after the manipulating lever 2 is strongly grasped, and causing the pressing portion 45 to swing, as illustrated in FIG. 20. When the manipulating lever 2 is grasped and turned in the closing direction in this state, the latch portion 15 of the latch piece portion 7 is pushed against the latch receiving member 16(a). Thus, the slit 75 is compressed so as to be elastically deformed. Then, the latch portion 15 is turned more downwardly due to elastic effects. Thus, the latch portion 15 is latched to the latch receiving portion 16. Even when a force applied to the pressing portion 45 and the manipulating lever 2 is released, the latched state is held. Consequently, neither the latch member 15A nor the manipulating lever 2 returns to the initial position.

Further, the pressing portion 45 is flush with the outer surface of the rear surface portion of the stapler body 1. Consequently, the pressing portion 45 cannot be drawn out by a finger. Thus, the medical stapler is held in the closed state. Accordingly, the medical stapler can be safely discarded.

Incidentally, upon completion of suturing a wound, similarly, the latch portion 15 can be latched to the latch receiving portion 16 by grasping the manipulating lever 2 after the pressing portion 45 is preliminarily put into a pushed state.

Third Exemplary Embodiment

Figure 21:
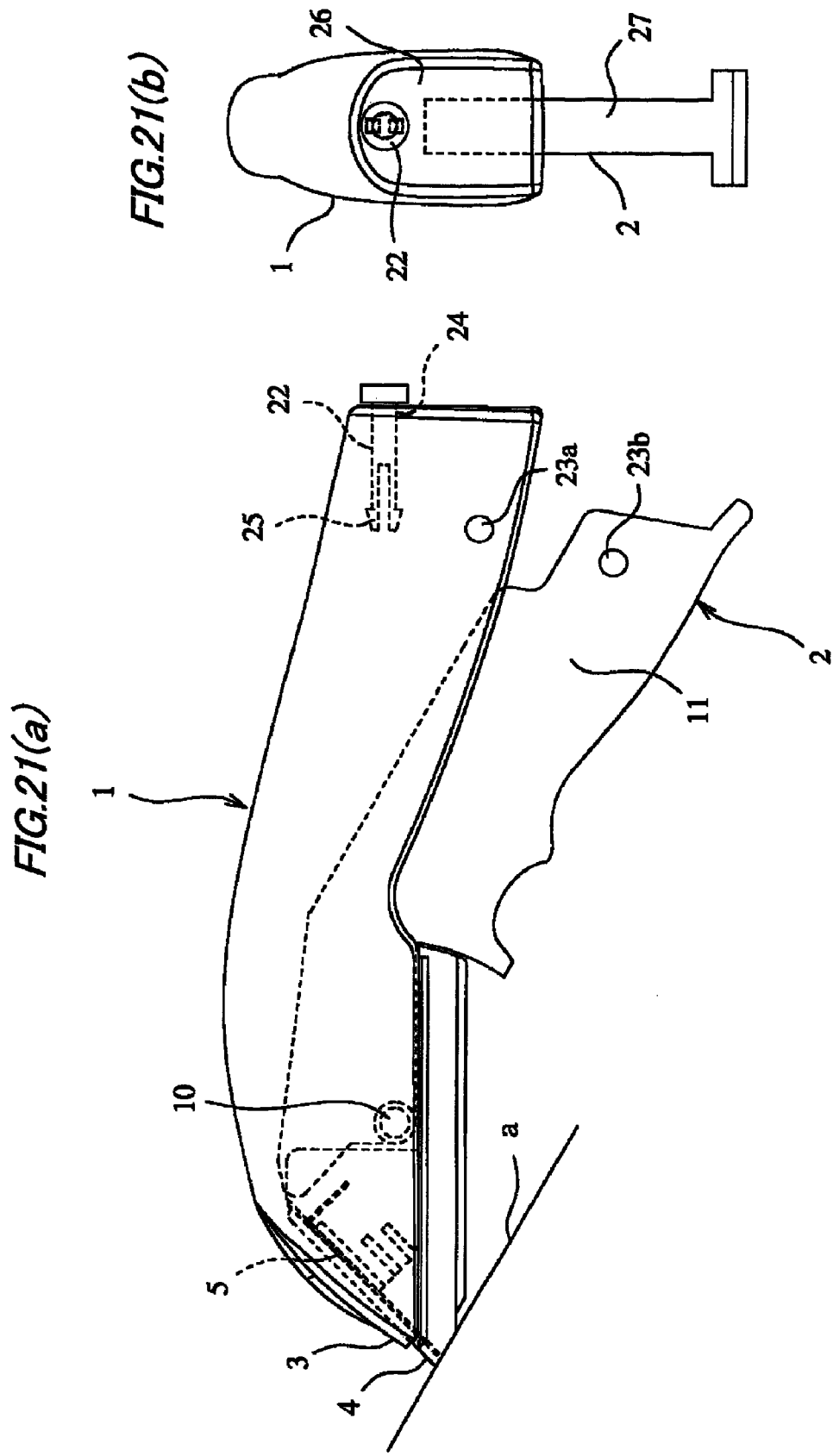
FIG. 21(a) is a side view of a stapler according to a third exemplary embodiment.
FIG. 21(b) is a rear view of the stapler illustrated in FIG. 21(a).

FIGS. 21(a) and 21(b) illustrate a third exemplary embodiment. A latch pin 22 is attached to a stapler body 1.

In addition, pin holes 23a and 23b are formed in the stapler body 1 and a manipulating lever 2, respectively. The latch pin 22 functions as the latch portion. The pin hole 23b of the manipulating lever 2 functions as the latch receiving portion.

The diameters of the pin holes 23a and 23b are equal to each other. When the pin holes are aligned with each other, the latch pin 22 can be latched in the two pin holes 23a and 23b.

The latch pin 22 is provided in a state in which the latch pin 22 is inserted into a mounting hole 24 of a rear end wall 26 of the stapler body 1. A latch jaw 25 is formed by splitting a tip end part of the latch pin 22 into two parts.

With the aforementioned configuration, no problems occur even when the manipulating lever 2 is turned in the closing direction at normal suturing of a wound.

Figure 22:
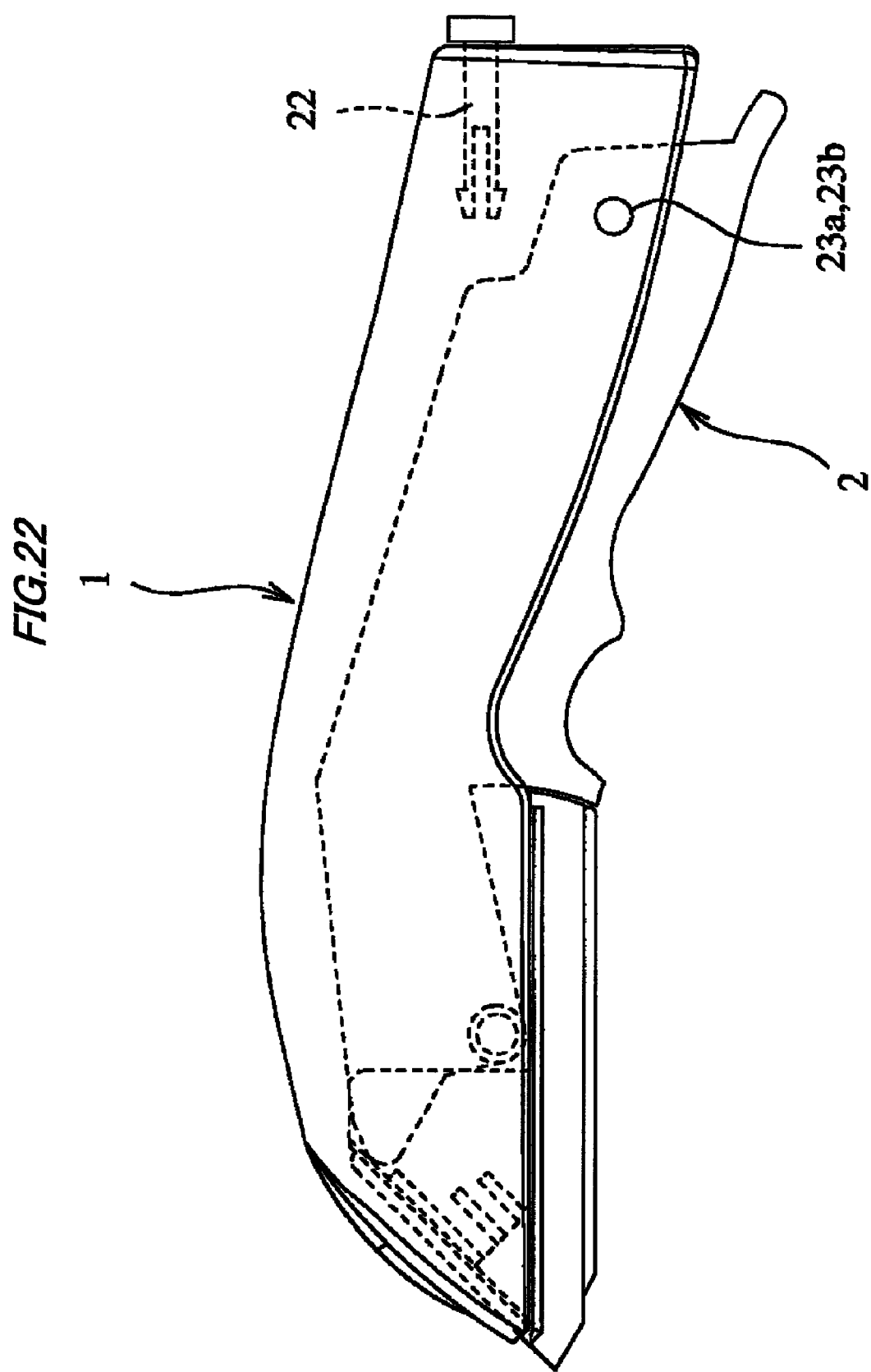
FIG. 22 is a side view of the stapler illustrated in FIG. 21(a) at a normal operation.
Figure 23B:
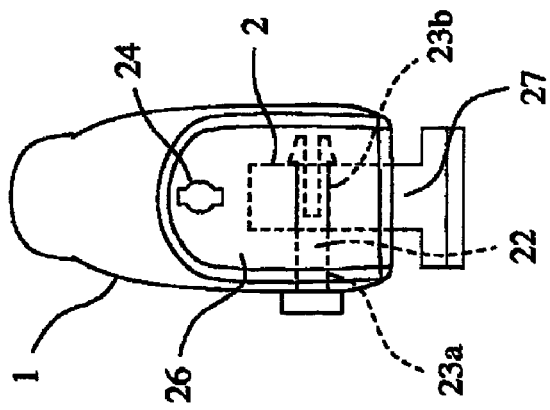
FIG. 23(b) is a side view illustrating a state of the medical stapler illustrated in FIG. 21(a), in which the medical stapler is discarded.
Figure 23A:
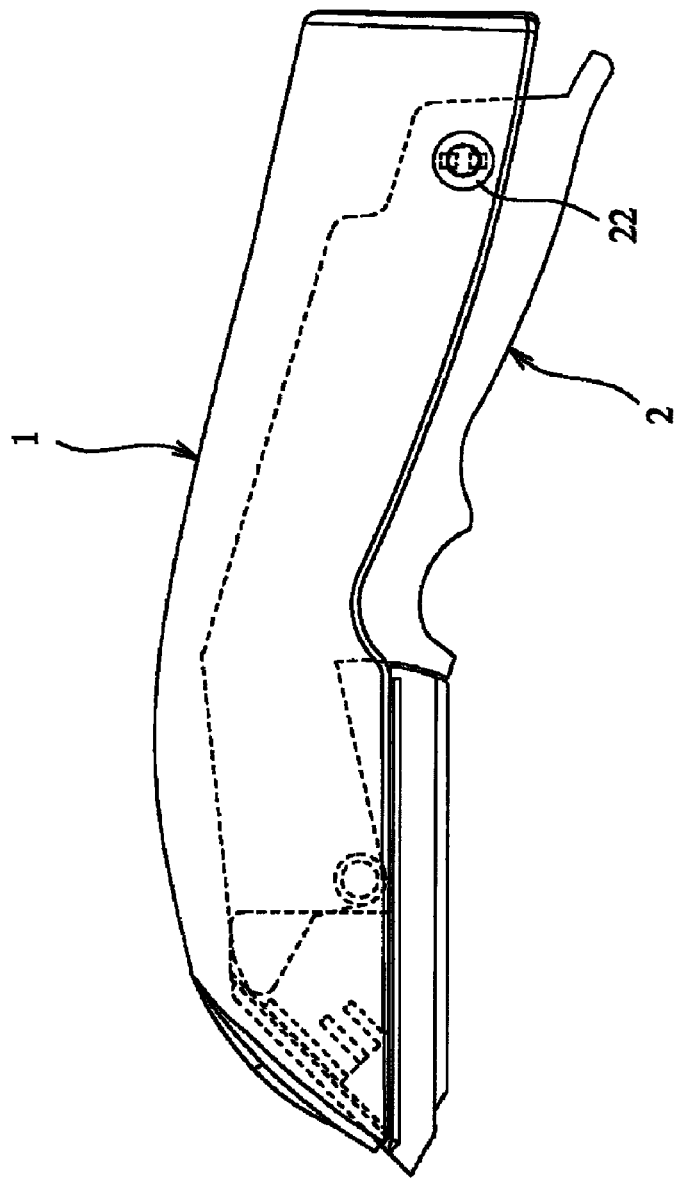
FIG. 23(a) is an enlarged cross-sectional view illustrating a state of the medical stapler illustrated in FIG. 21(a), in which the medical stapler is discarded.

When the medical stapler is discarded upon completion of suturing of all wounds, the latch pin 22 is extracted from the mounting hole 24 of the stapler body 1. Then, the manipulating lever 2 is turned in a closing direction in which the manipulating lever 2 is accommodated in an accommodating portion 8. The latch pin 22 is inserted into and is latched in the two pin holes 23a and 23b, as illustrated in FIGS. 23(a) and 23(b), in a state in which the pin holes 23a and 23b respectively formed in the stapler body 1 and the manipulating lever 2 are aligned with each other, as illustrated in FIG. 22. Because the latch pin 22 is provided in the stapler in a state in which the latch pin 22 is attached to the stapler body 1, the extraction of the latch pin 22 can easily be performed.

Further, the medical stapler can easily be operated.

Incidentally, the latch pin 22 can be attached to the manipulating lever 2. Alternatively, the latch pin 22 can be included in a package for packaging the medical stapler.

Further, the pin holes can be formed in the rear end wall 26 of the stapler body 1 and a rear end wall 27 of the manipulating lever 2, respectively. In this case, the latch pin is inserted from the rear of the stapler into the pin holes and is latched therein.

Fourth Exemplary Embodiment

FIGS. 24(a) and 24(b) illustrate a fourth exemplary embodiment configured so that a latch groove 28 is formed in a manipulating lever 2, and that a stapler body 1 is provided with a slide shaft 30 which is latchable to the latch groove 28 when the manipulating lever 2 is turned in a closing direction, in which the manipulating lever 2 is accommodated in the accommodating portion 8, upon completion of the suturing of a wound. The slide shaft 30 functions as the latch portion, while the latch groove 28 functions as the latch receiving portion. A first slide groove 31 elongated in a direction intersecting with a turning direction of the manipulating lever 2 is formed in the stapler body 1. The slide shaft 30 is provided in the first slide groove 31 such that the slide shaft 30 is externally operated to cause the slide shaft 30 to slide. On the other hand, a substantially L-shaped groove, in which a second slide groove 32 extending along the turning direction is continued to a latch groove 28 elongated in the same direction as that of the first slide groove 31, is formed in the manipulating lever 2. The first slide groove 31 and the second slide groove 32 are formed so that when the manipulating lever 2 is turned, a front end portion of the first slide groove 31 overlaps with the second slide groove 32.

Figure 25:
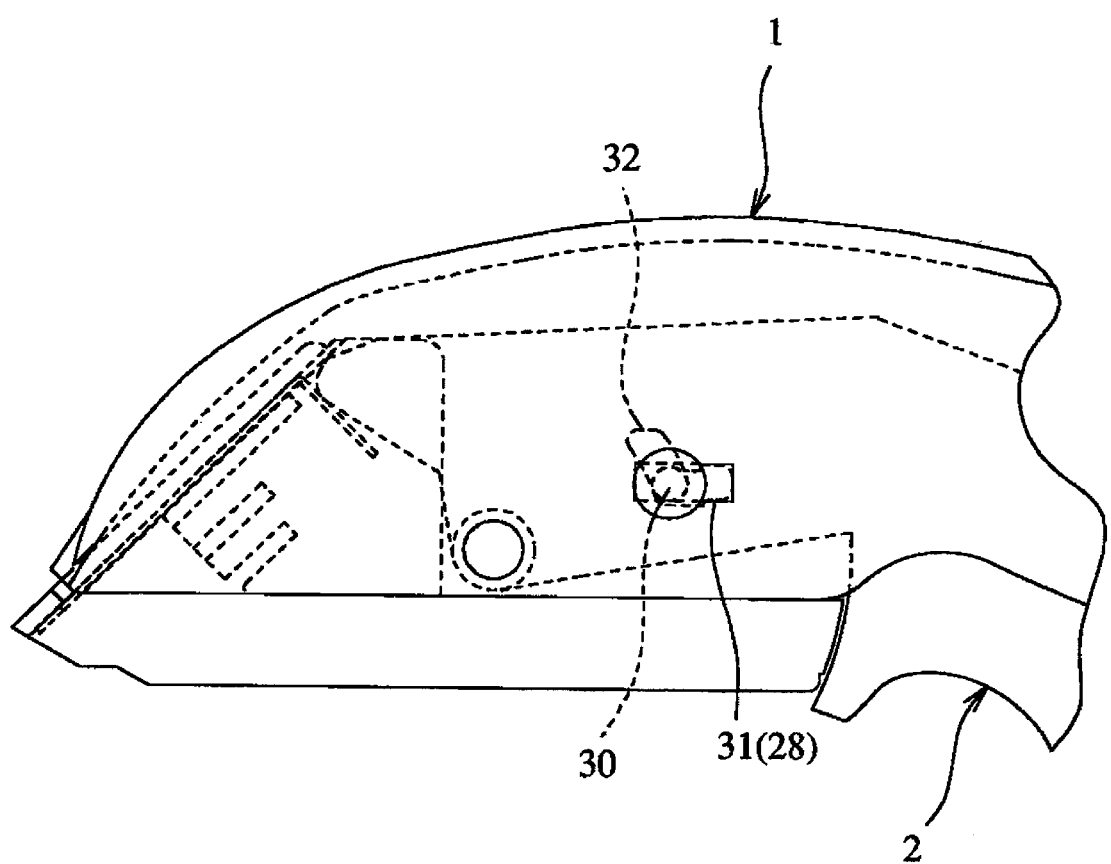
FIG. 25 is a side view of the medical stapler illustrated in FIG. 24(a) at a normal operation.

With the aforementioned configuration, in a normal suturing operation, the slide shaft 30 only slides at an end portion of the first slide groove 31 along the second slide groove 32, as illustrated in FIG. 25. When the medical stapler is discarded upon completion of suturing of the wound, it is sufficient to latch the slide shaft 30 in the latch groove 28 by turning the manipulating lever 2 in the closing direction, in which the manipulating lever 2 is accommodated in the accommodating portion 8, as illustrated in FIGS. 26(a) and 26(b), to thereby slide the slide shaft 30 along the first slide groove 31 towards an opposite side. Consequently, the closed state of the manipulating lever 2 is held. Because it is unnecessary to detach the slide shaft 30 therefrom, the medical stapler can be operated extremely easily.

Further, FIGS. 27(a) and 27(b) illustrate an example of providing the slide shaft 30 to be enabled to slide a direction differing from the direction in which the slide shaft 30 is slid in the aforementioned example. A slide groove 33 elongated in the turning direction of the manipulating lever 2 is formed in the rear end wall of the manipulating lever 2. The latch groove 28, which is cross-sectionally circular-shaped and has a large groove width, is formed in the bottom of the slide groove 33. On the other hand, the slide shaft 30 is attached in the rear end wall 26 of the stapler body 1 movably in a mediolateral direction (or anteroposterior direction). A small-diameter portion 30a is formed at a leading end side of the slide shaft 30, while a large-diameter portion 30b is formed at the base part thereof. The small-diameter portion 30a and the large-diameter portion 30b are formed so that the diameter of the small-diameter portion 30a is slightly smaller than the groove width of the slide groove 33, and that the diameter of the large-diameter portion 30b is slightly smaller than the diameter of the latch groove 28 provided at the bottom of the slide groove 33 and is larger than the groove width of the slide groove 33.

In the aforementioned configuration, in a normal suturing operation, the small-diameter portion 30a of the slide shaft 30 is disposed to engage with the slide groove 33. Even when the manipulating lever 2 is opened and closed, the small-diameter portion 30a only slides along the slide groove 33. Thus, there are no problems. On the other hand, when the medical stapler is discarded upon completion of suturing of a wound, the manipulating lever 2 is turned in the closing direction, in which the manipulating lever 2 is accommodated in the accommodating portion 8, as illustrated in FIGS. 28(a) and 28(b). When the latch portion 15 in the slide groove is aligned with the slide shaft 30, the slide shaft 30 is axially slid by being pressed. Thus, the large-diameter portion 30b is latched to the latch groove 28. Consequently, the manipulating lever 2 is latched and cannot be operated in an opening direction.

It is unnecessary to detach the slide shaft 30 therefrom when the manipulating lever 2 is latched. Accordingly, the medical stapler can be operated extremely easily.

Incidentally, the medical stapler can be modified so that reversely to the aforementioned example, the latch groove is provided in the stapler body 1, while the slide shaft is provided in the manipulating lever 2.

Meanwhile, FIG. 29 illustrates another example configured so that the latch groove 28 is formed in the manipulating lever 2, and that the stapler body 1 is provided with the slide shaft 30 which is latchable in the latch groove 28 when the manipulating lever 2 is turned in the closing direction upon completion of the suturing of a wound. The slide groove 31 elongated in a direction intersecting with the turning direction of the manipulating lever 2 is formed in the stapler body 1. On the other hand, in the front part of the grip portion 11 of the manipulating lever 2, a frontwardly opened latch groove 28 is formed in a middle portion of an edge part 2a formed along a circular arc around the turning shaft 10 of the manipulating lever. The latch groove 28 includes a groove bottom portion 28a formed to have a diameter, which is substantially equal to the shaft diameter of the slide shaft 30, and a narrow portion 28b which is placed closer to an aperture portion than the groove bottom portion and which is formed to have a diameter narrower than the shaft diameter of the slide shaft.

With the aforementioned configuration, a normal suturing operation is performed without operating the slide shaft 30.

Figure 30:
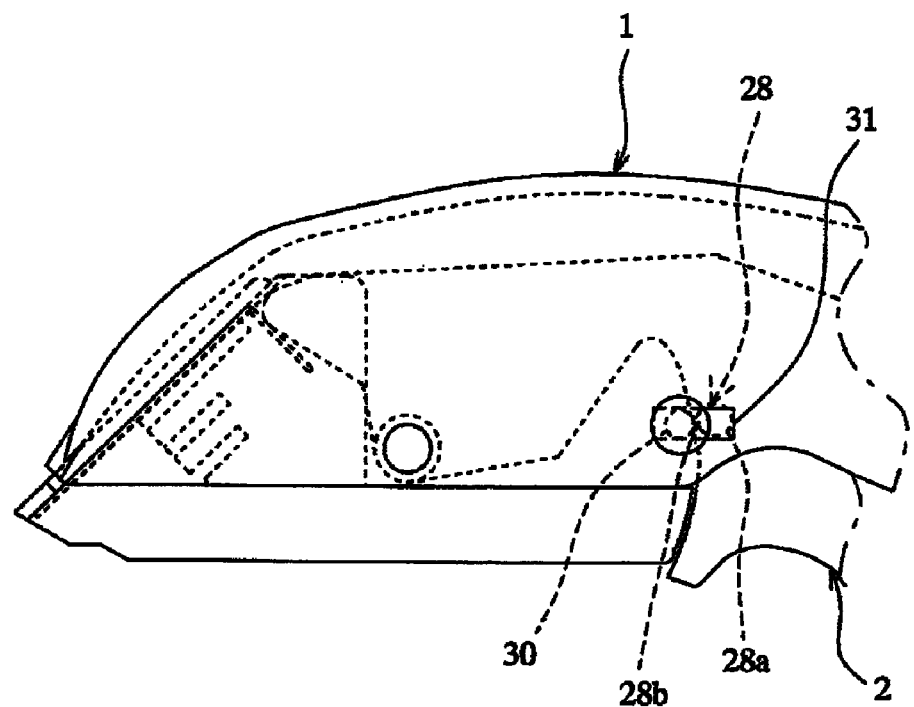
FIG. 30 is an enlarged side view illustrating a state in which a latch groove and a slide groove are aligned with each other at disposal of the medical stapler illustrated in FIG. 29.
Figure 31:
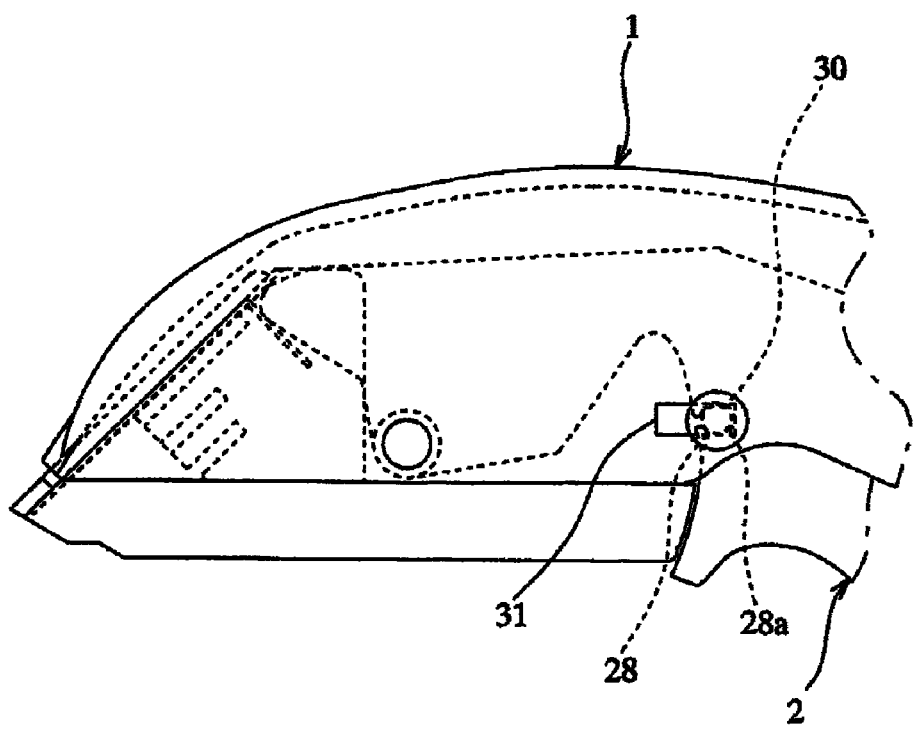
FIG. 31 is an enlarged side view illustrating a state in which the medical stapler illustrated in FIG. 29 is discarded.

Opening and closing operations of the manipulating lever 2 can be freely performed to perform the suturing operation. On the other hand, when the medical stapler is discarded upon completion of a suturing operation, the manipulating lever 2 is grasped and put into a closed state in which the slide groove 31 and the latch groove 28 are aligned with each other, as illustrated in FIGS. 30 and 31. Then, the slide shaft 30 is forcibly moved to the latch groove 28 along the slide groove 31. The slide shaft 30 is latched to the groove bottom portion 28a after the narrow portion 28b provided at an aperture side of the slide groove 31 is spread. Thus, the closed state of the manipulating lever 2 can be held. Further, when the slide shaft 30 is slid in an opposite direction, it is necessary to spread the narrow portion 28b. Thus, there is no fear that the slide shaft 30 is erroneously slid in a normal suturing operation. Consequently, the slide shaft 30 is put into a latched state in which the slide shaft 30 is latched in the latch groove 28. It is unnecessary to detach the slide shaft 30 therefrom. Accordingly, the medical stapler can easily be handled.

Incidentally, the configuration according to the present embodiment, in which the narrow portion is formed in the aperture side of the latch groove 28, is not limited to the aforementioned example. For example, the medical stapler can be constructed so that a non-return member (not shown) is provided on the inner side of the latch groove thereby allowing the slide shaft to enter the latch groove and inhibiting the slide shaft from detaching from the latch groove.

Fifth Exemplary Embodiment

Figure 32A:
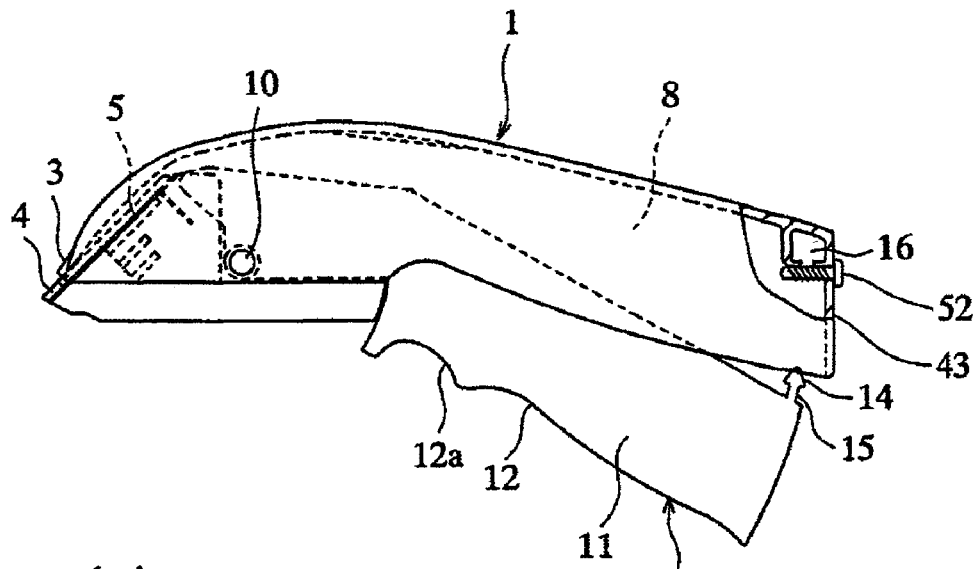
FIG. 32(a) is a side view partly cross-sectionally illustrating an initial state of a stapler according to a fifth exemplary embodiment.
Figure 32B:
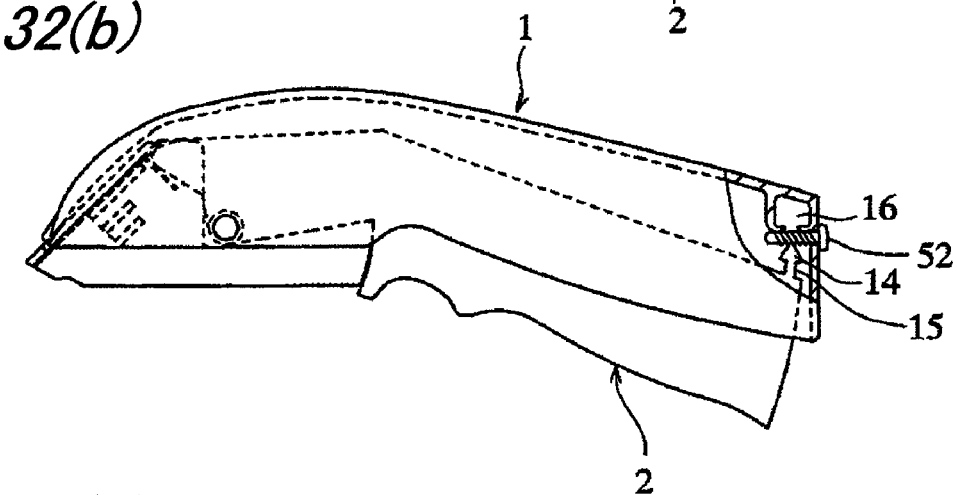
FIG. 32(b) is a side view partly cross-sectionally illustrating the stapler according to the fifth exemplary embodiment at a normal operation.
Figure 32C:
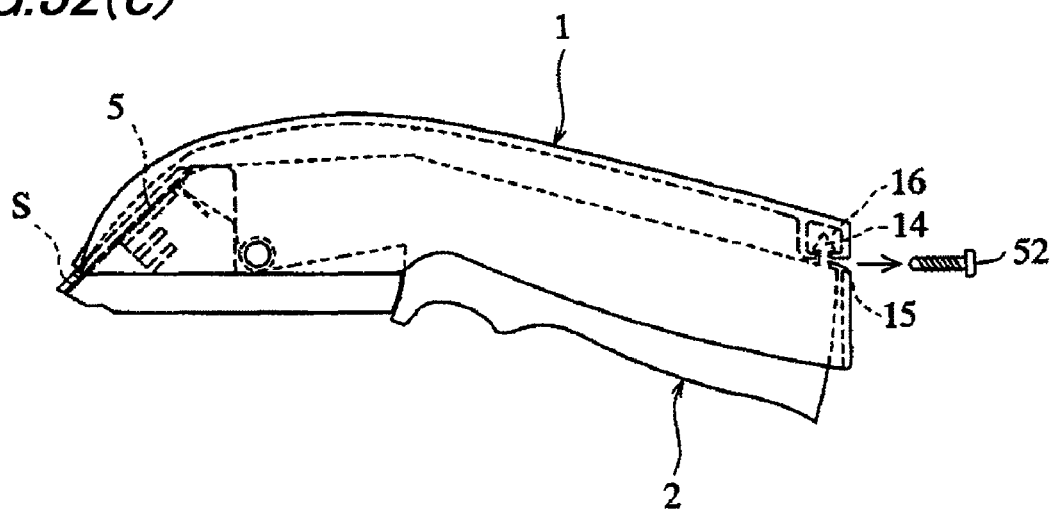
FIG. 32(c) is a side view illustrating an operating state of the stapler according to the fifth exemplary embodiment at disposal thereof.

FIGS. 32(a), 32(b), and 32(c) illustrate a fifth exemplary embodiment. A latch portion 15 having a latch jaw 14 is formed on the upper rear end portion of the manipulating lever 2 to upwardly protrude therefrom. On the other hand, a dovetail-groove-like latch receiving portion 16 is formed on an upper part of the accommodating portion 8 of the stapler body 1 to be downwardly opened. Further, the latch portion 15 is formed latchably to the latch receiving portion 16 when the manipulating lever 2 is turned in the closing direction in which the manipulating lever 2 is accommodated in the accommodating portion 8.

Moreover, an interference member 52 is provided between the latch portion 15 and the latch receiving portion 16. The interference member 52 is detachably and attachably attached to the rear surface portion 43 of the stapler body 1 by screwing.

A position, at which the interference member 52 is attached thereto by being deeply screwed, is set as a first position (position illustrated in FIG. 32(a)), while a position, at which the interference member 52 is detached therefrom, is set as a second position (position illustrated in FIG. 32(c)).

Moreover, the medical stapler is constructed so that at the first position, the interference member 52 traverses across a front of an aperture part of the latch receiving portion 16 to prevent the latch portion 15 from being latched to the latch receiving portion 16. On the other hand, at the second position at which the interference member 52 is retreated from the aperture part, the latching between the latch portion 15 and the latch receiving portion 16 is allowed.

An operation mode of the medical stapler is described below. A normal suturing operation is performed by fixing the interference member 52 to the rear surface portion 43 through screwing and by placing the interference member 52 at the first position. In this case, after staples are driven out by operating the manipulating lever 2 in the closing direction (staple driving direction), as illustrated in FIG. 32(b), even when the medical stapler is operated any more, the leading end of the latch portion 15 abuts against the interference member 52. Thus, the medical stapler cannot move more upwardly. Therefore, the latch portion 15 cannot latch the latch portion 15 to the latch receiving portion 16. When a force applied to the manipulating lever 2 is released upon completion of a closing operation, the manipulating lever 2 is operated in the downward opening direction, preparations for the next suturing operation are made.

On the other hand, when the medical stapler is discarded upon completion of the suturing operation, the interference member 52 is detached therefrom as illustrated in FIG. 32(c)

Further, the interference member 52 is moved to the second position at which the interference member 52 is retreated from the front of the latch receiving portion 16. When the manipulating lever 2 is grasped in this state and is turned in the closing direction, the latch portion 15 enters the latch receiving portion 16 and passes therethrough. Thus, the latch jaw 14 is latched to the latch receiving portion 16. Accordingly, even when a force applied to the manipulating lever 2 is released, the latched state is held. Further, the manipulating lever 2 does not return to the initial position. Consequently, the medical stapler is held in the closed state. The interference member 52 is detached from the stapler body 1. Thus, it is advisable to discard the interference member 52 together with the stapler body 1.

As described above, upon completion of the suturing operation, the medical stapler is held in the closed state.

Thus, the medical stapler can be discarded in a safe state.

Moreover, unless the interference member 52 is operated, the latch portion 15 cannot be latched to the latch receiving portion 16. Consequently, there is no fear that the manipulating lever 2 is erroneously held in the closing state.

Incidentally, reversely to the aforementioned embodiment, the latch portion 15 and the latch receiving portion 16 can be constructed so that the downward latch portion is formed in the stapler body 1, while the latch receiving portion latchable to the latch portion 15 is formed in the manipulating lever 2.

Figure 33A:
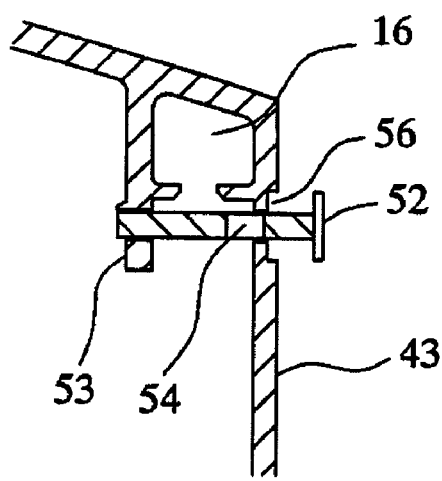
FIG. 33(a) is a partly cross-sectionally enlarged view of a stapler body, which illustrates another example of an interference member (at a first position).
Figure 33B:
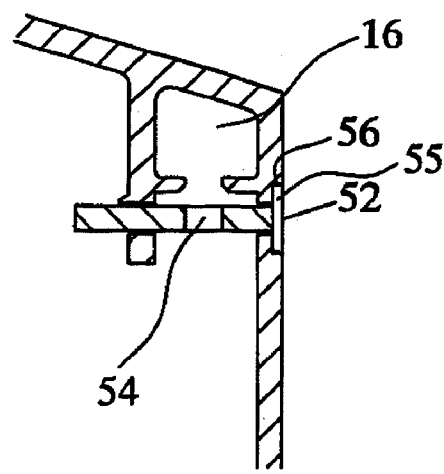
FIG. 33(b) is a partly cross-sectionally enlarged view illustrating a second position of the interference member illustrated in FIG. 33(a).

Furthermore, as illustrated in FIGS. 33(*a*) and 33(*b*), the interference member 52 can be provided to be able to be inserted into and removed from the rear surface portion 43 and a support wall 53 formed to be pendent from the rear of the top surface portion of the stapler body 1. In addition, a penetration opening portion 54, through which the latch portion 15 passes, is formed in the interference member 52. The medical stapler can be adapted so that the interference member 52 is moved to the first position illustrated in FIG. 33(*a*) and the second position illustrated in FIG. 33(*b*) according to an insertion depth of the interference member 52. Incidentally, the drawing of the manipulating lever 2 and the latching portion 15 are omitted therein.

According to the aforementioned configuration, a normal suturing operation is performed by placing the interference member 52 in the first position. In this case, when a user tries to further operate the manipulating lever 2 after staples are driven out by operating the manipulating lever 2 in the closing direction (staple driving direction), the leading end of the latch portion 15 abuts against the interference member 52. Thus, the latch portion 15 cannot move more upwardly. Consequently, the latch portion 15 cannot be latched to the latch receiving portion 16. Thus, when a fore applied to the manipulating lever 2 is released after the closing operation is performed, the manipulating lever 2 is operated in the downward opening direction.

On the other hand, when the disposal of the medical stapler is performed upon completion of the suturing operation, the interference member 52 is moved to the second position, at which the penetration opening portion 54 of the interference member 52 and the aperture portion of the latch receiving portion 16 are aligned with each other, by being pushed. When the manipulating lever 2 is grasped and is turned in the closing direction, the latch portion 15 penetrates through the penetration opening portion 54 and enters the latch receiving portion 16. Thus, the latch jaw 14 is latched to the latch receiving portion 16. Consequently, even when a force applied to the manipulating lever 2 is released, the latched state is held. The manipulating lever 2 does not return to the initial position. Accordingly, the medical stapler is held in the closed state. At that time, the interference member 52 remains attached to the stapler body 1. Thus, it is advisable to discard the interference member 52 together with the stapler body 1.

Incidentally, preferably, a concave portion 56 for accommodating a head portion 55 of the interference member 52 is preliminarily formed in the rear surface portion 43.

Alternatively, a position, at which the interference member 52 is deeply inserted, and a position, at which the interference member 52 is drawn out and is shallowly inserted, can be set as the first position and the second position, respectively, by appropriately changing the position, at which the penetration opening portion 54 is provided.

Figure 34A:
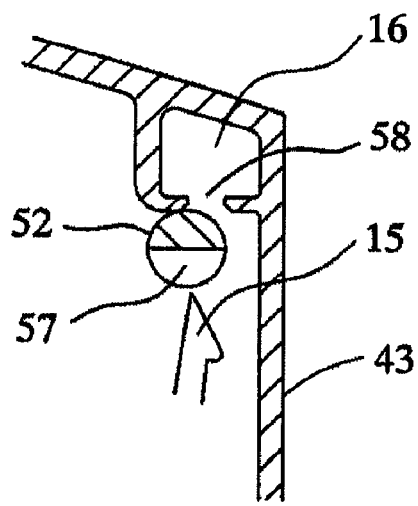
FIG. 34(a) is a partly cross-sectionally enlarged view of a stapler body, which illustrates still another example of the interference member (at the first position).
Figure 34B:
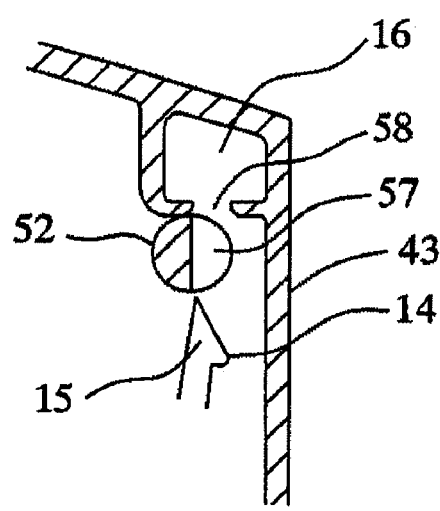
FIG. 34(b) is a partly cross-sectionally enlarged view illustrating a second position of the interference member illustrated in FIG. 34(a).

The first position and the second position according to the present embodiment are not limited to those set in the configuration in which the interference member 52 is moved in a rectilinear movement direction as illustrated in FIGS. 34(*a*) and 34(*b*). The medical stapler according to the invention can have a configuration in which the interference member 52 is provided between the latch portion 15 and the latch receiving portion 16, and in which the interference member 52 performs rotational movement between the first position and the second position. The interference member 52 is cylindrically shaped.

Both ends of the interference member 52 are rotatably supported on a side surface portion of the stapler body 1. Although not shown, a rotary knob is formed integrally with the exterior of the interference member 52. Furthermore, a cross-sectionally crescentically-shaped cutout is formed in a part of the interference member 52, which corresponds to the aperture portion of the latch receiving portion 16. As illustrated in FIG. 34(*a*), a position at which the interference member 52 blocks up the aperture portion of the latch receiving portion 16, and a position at which a cutout portion 57 releases an opening portion 58 of the latch receiving portion 16, are set as the first position and the second position, respectively.

Accordingly, when the interference member 52 is placed at the first position, the opening portion 58 of the latch receiving portion 16 is blocked. Thus, the latch portion 15 is prevented from being latched thereto. On the other hand, when the interference member 52 is placed at the second position, the opening portion 58 is released. Thus, the latching between the latch portion 15 and the latch receiving portion 16 is allowed. Additionally, the latch jaw 14 is formed in one side of the latch portion 15.

With the aforementioned configuration, a normal suturing operation is performed by placing the interference member 52 at the first position. In this case, after staples are driven out by operating the manipulating-lever 2 in the closing direction (staple driving direction), even when a user tries to further operate the medical stapler, the leading end of the latch portion 15 abuts against the interference member 52. Thus, the medical stapler cannot move more upwardly. Therefore, the latch portion 15 cannot latch the latch portion 15 to the latch receiving portion 16. When a force applied to the manipulating lever 2 is released upon completion of a closing operation, the manipulating lever 2 is operated in the downward opening direction, and preparations for the next suturing operation are made.

On the other hand, when disposal of the medical stapler is performed upon completion of the suturing operation, the interference member 52 is moved to the second position, at which the interference member 52 is retreated from the front of the opening portion 58 of the latch receiving portion 16, by being rotated. When the manipulating lever 2 is grasped and turned in the closing direction in this state, the latch portion 15 enters and penetrates the inside of the latch receiving portion 16, and the latch jaw 14 is latched to the latch receiving portion 16. Thus, even when a force applied to the manipulating lever 2 is released, the latched state is held. The manipulating lever 2 does not return to an initial position. The medical stapler is held in the closed state. Thus, the medical stapler can be discarded in a safe state. Further, unless the interference member 52 is operated, the interference member 52 is not operated to the latchable position. Consequently, there is no fear that the manipulating lever 2 is erroneously held in the closed state.

Incidentally, reversely to the aforementioned embodiment, the latch portion 15 and the latch receiving portion 16 are configured such that the downward latch portion is formed at the stapler body 1, and that the latch receiving portion latchable to the latch portion is formed in the manipulating lever 2.

Sixth Exemplary Embodiment

FIGS. 35(*a*) and 35(*b*) illustrate a sixth exemplary embodiment. As illustrated in FIG. 35(*b*), an L-shaped latch hook 34 is upwardly and downwardly turnably attached to the rear end wall 26 of the stapler body 1. On the other hand, a latch pin 16 is formed on the rear end wall 27 of the manipulating lever 2 to protrude therefrom. The latch hook 34 functions as the latch portion.

In the aforementioned configuration, during a normal suturing operation, the latch hook 34 is not latched to the latch pin 16. Thus, even when the manipulating lever 2 is opened and closed, there are no problems.

On the other hand, when the disposal of the medical stapler is performed upon completion of a suturing operation, the manipulating lever 2 is turned in the closing direction, in which the manipulating lever 2 is accommodated in the accommodating portion 8, as illustrated in FIGS. 36(a) and 36(b), to thereby turn and latch the latch hook 34 to the latch pin 16. Consequently, the manipulating lever 2 is latched.

The manipulating lever 2 cannot operate in the opening direction.

Figures 38A, 38B:
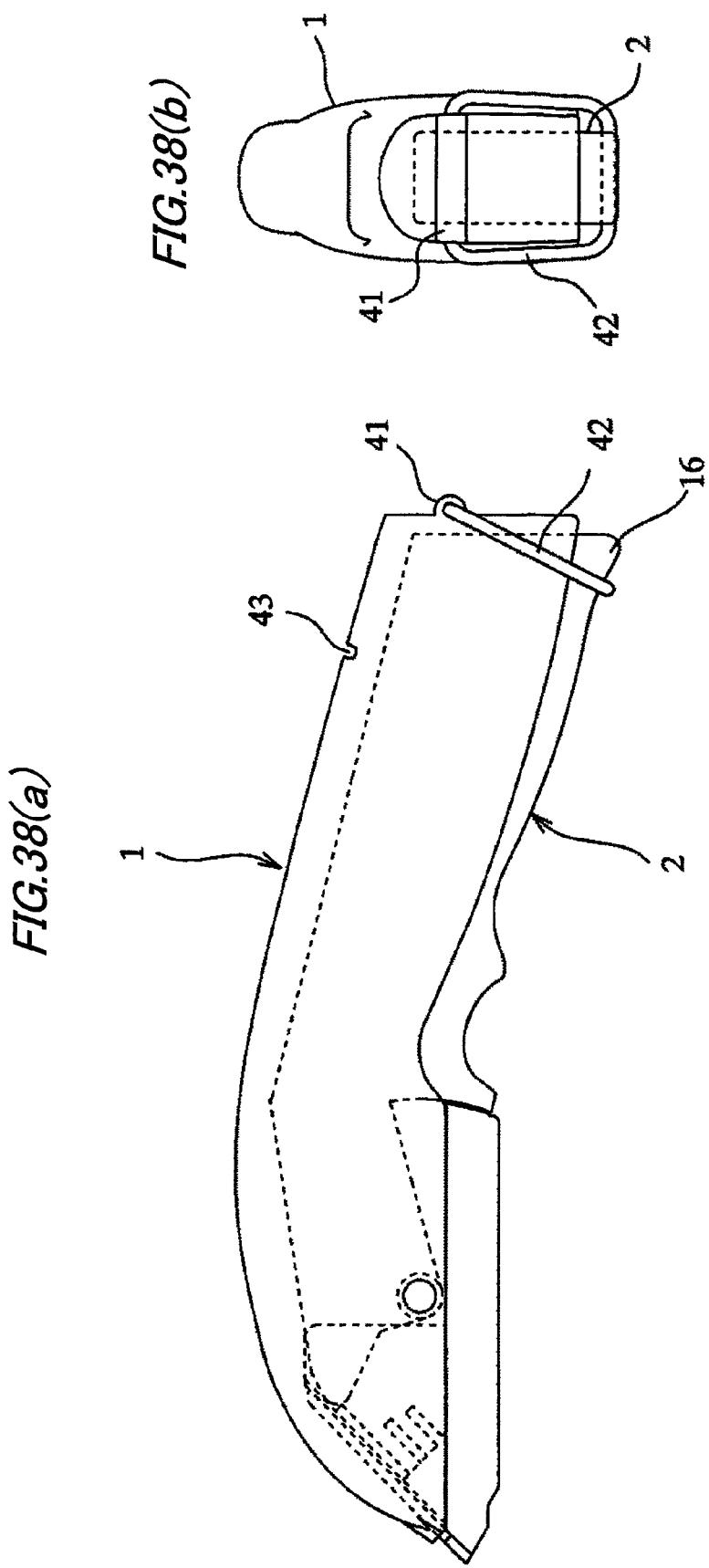
FIG. 38(a) is a side view illustrating a state in which the medical stapler illustrated in FIG. 37(a) is discarded.
FIG. 38(b) is a rear view illustrating a state in which the medical stapler illustrated in FIG. 37(a) is discarded.

FIGS. 37(a) and 37(b) illustrate yet another example of the embodiment. As illustrated in FIGS. 37(a) and 37(b), a projection portion 41 is formed in the rear end wall 26 of the stapler body 1. Concave portions are formed in both side parts of the projection portion 41, respectively. End portions of substantially C-shaped ring-like latch hook 42 are inserted into the concave portions, respectively. The latch hook 42 is supported by the projection portion 41 turnably in an anteroposterior direction. The latch hook 42 functions as the latch portion. A concave groove 43, into which the latch hook 42 can be fit, is formed in the upper portion of the stapler body 1. The stapler having the aforementioned configuration in a state, in which the latch hook 42 is fit into the concave groove 43, is used in a normal suturing operation as the medical stapler. Further, when the medical stapler is discarded, the manipulating lever 2 is held in the closed state by turning the latch hook 42, and by latching the manipulating lever 2 using the latch hook 42, as illustrated in FIGS. 38(a) and 38(b). In this case, the manipulating lever 2 itself functions as the latch receiving portion.

Incidentally, the medical stapler can be constructed so that a concave groove (not shown), into which the latch hook 42 is fit, is preliminarily formed in the manipulating lever 2. When the medical stapler is discarded, the disposal thereof can be performed in a state in which the latch hook 42 is fit into the concave groove formed in the manipulating lever 2.

Although the invention has been described in detail with reference to the specific embodiments, it is apparent to those skilled in the art that the invention can be changed or modified in various manners without departing from the spirit and scope of the invention.

The present application is based on Japanese Patent Application (Patent Application No. 2006-182370) filed on Jun. 30, 2006, Japanese Patent Application (Patent Application No. 2006-340593) filed on Dec. 18, 2006, and Japanese Patent Application (Patent Application No. 2007-015988) filed on Jan. 26, 2007, and the contents of which are incorporated herein by reference.

INDUSTRIAL APPLICABILITY

The invention is applicable to a medical stapler used to suture a wound.

The invention claimed is:

1. A medical stapler comprising:
   a stapler body having a head portion for driving out a medical staple and provided at one end of the stapler body;
   a manipulating lever pivotally supported by the stapler body to be closable and openable so that a grip portion placed at a side of the manipulating lever, which is opposite to a side thereof corresponding to the head portion, is urged in an opening direction in which the grip portion is moved apart from the stapler body, and that when the medical staple is driven out, the manipulating lever is turned in a closing direction, in which the manipulating lever is moved closer to the stapler body, to protrude the staple from the head portion to suture a wound while both side tip end portions of the staple are inwardly bent, wherein the manipulating lever is enabled to be latched in the stapler body in a state, in which the manipulating lever is turned in the closing direction of bending the medical staple, upon completion of suturing of the wound;
   a latch portion provided on one of the stapler body and the manipulating lever;
   a latch receiving portion provided on the other of the stapler body and the manipulating lever, wherein the manipulating lever is latched to the stapler body by the latch portion and the latch receiving portion, and wherein one of the latch portion and the latch receiving portion is operable between a standby position at which the one of the latch portion and the latch receiving portion is prevented from being latched to the other of the latch portion and the latch receiving portion, and a latchable position at which the one of the latch portion and the latch receiving portion is allowed to be latched to the other of the latch portion and the latch receiving portion;
   an operating portion provided on an outer surface of the stapler body; and
   a latch piece portion extended from the operating portion to an inner side of the stapler body,
   wherein one of the latch portion and the latch receiving portion is provided in the latch piece portion, and
   wherein the latch piece portion is operated from the standby position to the latchable position.

2. The medical stapler according to claim 1,
   wherein the latch portion is provided on the manipulating lever,
   wherein the latch receiving portion is provided in the stapler body, and
   wherein, when the manipulating lever is turned in the closing direction upon completion of the suturing of the wound, the latch portion is latched to the latch receiving portion by turning the manipulating lever over a movable range to elastically deform the manipulating lever.

3. The medical stapler according to claim 1, further comprising:
   a holding means configured to hold one of the latch portion and the latch receiving portion at the standby position and the latchable position.

4. The medical stapler according to claim 1, wherein latching between the latch portion and the latch receiving portion is allowed by turning the manipulating lever in the closing direction after the operating portion is operated.

5. The medical stapler according to claim 1, wherein latching between the latch portion and the latch receiving portion is allowed by operating the operating portion after the manipulating lever is turned in the closing direction.

6. A medical stapler comprising:
   a stapler body having a head portion for driving out a medical staple and provided at one end of the stapler body;
   a manipulating lever pivotally supported by the stapler body to be closable and openable so that a grip portion placed at a side of the manipulating lever, which is opposite to a side thereof corresponding to the head portion, is urged in an opening direction in which the grip portion is moved apart from the stapler body, and that when the medical staple is driven out, the manipulating lever is turned in a closing direction, in which the manipulating lever is moved closer to the stapler body, to protrude the staple from the head portion to suture a wound while both side tip end portions of the staple are inwardly bent, wherein the manipulating lever is enabled to be latched in the stapler body in a state, in which the manipulating lever is turned in the closing direction of bending the medical staple, upon completion of suturing of the wound;

a latch portion provided on one of the stapler body and the manipulating lever; and a latch receiving portion provided on the other of the stapler body and the manipulating lever, wherein the manipulating lever is latched to the stapler body by the latch portion and the latch receiving portion, wherein the latch portion comprises a latch pin, wherein the latch receiving portion comprises a first pin hole formed in the stapler body, wherein a second pin hole is provided in the manipulating lever, and wherein the latch pin is insertable into the first pin hole and the second pin hole in a state in which the first pin hole and the second pin hole are aligned with each other by turning the manipulating lever in the closing direction upon completion of the suturing of the wound.

7. A medical stapler comprising:

a stapler body having a head portion for driving out a medical staple and provided at one end of the stapler body;

a manipulating lever pivotally supported by the stapler body to be closable and openable so that a grip portion placed at a side of the manipulating lever, which is opposite to a side thereof corresponding to the head portion, is urged in an opening direction in which the grip portion is moved apart from the stapler body, and that when the medical staple is driven out, the manipulating lever is turned in a closing direction, in which the manipulating lever is moved closer to the stapler body, to protrude the staple from the head portion to suture a wound while both side tip end portions of the staple are inwardly bent, wherein the manipulating lever is enabled to be latched in the stapler body in a state, in which the manipulating lever is turned in the closing direction of bending the medical staple, upon completion of suturing of the wound;

a first slide groove formed in the stapler body and elongated in a direction intersecting with a turning direction of the manipulating lever;

an L-shaped groove formed in the manipulating lever, wherein the L-shaped groove is configured by a second slide groove extending along the turning direction and a latch groove elongated in the same direction as the first slide groove; and a slide shaft penetrating through both the first slide groove and the L-shaped groove.

8. A medical stapler comprising:

a stapler body having a head portion for driving out a medical staple and provided at one end of the stapler body;

manipulating lever pivotally supported by the stapler body to be closable and openable so that a grip portion placed at a side of the manipulating lever, which is opposite to a side thereof corresponding to the head portion, is urged in an opening direction in which the grip portion is moved apart from the stapler body, and that when the medical staple is driven out, the manipulating lever is turned in a closing direction, in which the manipulating lever is moved closer to the stapler body, to protrude the staple from the head portion to suture a wound while both side tip end portions of the staple are inwardly bent, wherein the manipulating lever is enabled to be latched in the stapler body in a state, in which the manipulating lever is turned in the closing direction of bending the medical staple, upon completion of suturing of the wound;

a latch portion provided on one of the stapler body and the manipulating lever; and a latch receiving portion provided on the other of the stapler body and the manipulating lever, wherein the manipulating lever is latched to the stapler body by the latch portion and the latch receiving portion, wherein the latch portion comprises a slide shaft, wherein the latch receiving portion comprises a latch groove, wherein the slide shaft is latchable in the latch groove when the manipulating lever is turned in the closing direction upon completion of the suturing of the wound, wherein the latch groove comprises an aperture portion, a groove bottom portion formed to have a diameter substantially equal to a shaft diameter of the slide shaft, and a narrow portion that is placed to the aperture portion and formed to be narrower than the shaft diameter of the slide shaft, and wherein the slide shaft is latched to the groove bottom portion by spreading the narrow portion.

9. A medical stapler comprising:

a stapler body having a head portion for driving out a medical staple and provided at one end of the stapler body;

a manipulating lever pivotally supported by the stapler body to be closable and openable so that a grip portion placed at a side of the manipulating lever, which is opposite to a side thereof corresponding to the head portion, is urged in an opening direction in which the grip portion is moved apart from the stapler body, and that when the medical staple is driven out, the manipulating lever is turned in a closing direction, in which the manipulating lever is moved closer to the stapler body, to protrude the staple from the head portion to suture a wound while both side tip end portions of the staple are inwardly bent, wherein the manipulating lever is enabled to be latched in the stapler body in a state, in which the manipulating lever is turned in the closing direction of bending the medical staple, upon completion of suturing of the wound;

a latch portion provided on one of the stapler body and the manipulating lever;

a latch receiving portion provided on the other of the stapler body and the manipulating lever, wherein the manipulating lever is latched to the stapler body by the latch portion and the latch receiving portion; and an interference member provided between the latch portion and the latch receiving portion to be positionable at a first position at which latching between the latch portion and the latch receiving portion is prevented and a second position at which the latching between the latch portion and the latch receiving portion is allowed.

10. A medical stapler comprising:

a stapler body having a head portion for driving out a medical staple and provided at one end of the stapler body;

a manipulating lever pivotally supported by the stapler body to be closable and openable so that a grip portion placed at a side of the manipulating thereof corresponding to the head portion, is urged in an opening direction in which the grip portion is moved apart from the stapler body, and that when the medical staple is driven out, the manipulating lever is turned in a closing direction, in which the manipulating lever is moved closer to the stapler body, to protrude the staple from the head portion to suture a wound while both side tip end portions of the staple are inwardly bent, wherein the manipulating lever is enabled to be latched in the stapler body in a state, in which the manipulating lever is turned in the closing direction of bending the medical staple, upon completion of suturing of the wound;

a latch portion provided on one of the stapler body and the manipulating lever; and a latch receiving portion provided on the other of the stapler body and the manipulating lever, wherein the manipulating lever is latched to the stapler body by the latch portion and the latch receiving portion, wherein the latch portion is a latch hook turnably provided at a rear portion of the stapler body, wherein the latch receiving portion is provided on the manipulating lever, and wherein the latch hook is latched to the latch receiving portion when the manipulating lever is turned in the closing direction upon completion of the suturing of the wound.

* * * * *